United States Patent [19]

Achard et al.

[11] Patent Number: 5,624,950

[45] Date of Patent: Apr. 29, 1997

[54] PERHYDROISOINDOLE DERIVATIVES AS SUBSTANCE P ANTAGONISTS

[75] Inventors: Daniel Achard, Thiais; Serge Grisoni, Choisy-le-Roi; Evelyne James-Surcouf, Lésigny; Jean-Luc Malleron, Marcoussis; Anne Morgat, Gentilly; Jean-François Peyronel, Palaiseau; Jean-François Sabuco, Thiais; Michel Tabart, Paris, all of France

[73] Assignee: Rhone-Poulenc Rorer S.A., Antony, France

[21] Appl. No.: 586,708

[22] PCT Filed: Jul. 28, 1994

[86] PCT No.: PCT/FR94/00952

§ 371 Date: Jan. 29, 1996

§ 102(e) Date: Jan. 29, 1996

[87] PCT Pub. No.: WO95/04040

PCT Pub. Date: Feb. 9, 1995

[30] Foreign Application Priority Data

Jul. 30, 1993 [FR] France .................. 93 09400
Oct. 7, 1993 [FR] France .................. 93 11846

[51] Int. Cl.$^6$ .................. C07D 209/44; A61K 31/40
[52] U.S. Cl. .................. 514/414; 514/300; 514/307; 514/314; 514/361; 514/397; 514/383; 514/372; 514/373; 546/122; 546/139; 546/174; 546/277.1; 548/127; 548/128; 548/181; 548/214; 548/215; 548/267.6; 548/312.1; 548/364.7; 548/455; 548/454; 548/465
[58] Field of Search .................. 548/455, 454, 548/465, 181, 214, 215; 546/122, 174, 139; 514/414, 300, 314, 361, 397

[56] References Cited

U.S. PATENT DOCUMENTS

| 5,102,667 | 4/1992 | Dubroeucq et al. |
| 5,112,988 | 5/1992 | Dubroeucq et al. |
| 5,451,601 | 9/1995 | Achard et al. ............ 514/416 |
| 5,484,804 | 1/1996 | Achard et al. ............ 514/414 |
| 5,508,433 | 4/1996 | Achard et al. ............ 548/515 |

FOREIGN PATENT DOCUMENTS

| 429366 | 5/1991 | European Pat. Off. |
| 430771 | 6/1991 | European Pat. Off. |
| 514274 | 11/1992 | European Pat. Off. |
| 514273 | 11/1992 | European Pat. Off. |
| WO93/21155 | 10/1993 | WIPO |
| WO93/21154 | 10/1993 | WIPO |

OTHER PUBLICATIONS

Derwent Abstract of EP–514273. (1992).
Derwent Abstract of EP–514274. (1992).

*Primary Examiner*—Jacqueline Haley
*Attorney, Agent, or Firm*—Finnegan, Henderson, Farabow, Garrett & Dunner, L.L.P.

[57] ABSTRACT

Perhydroisoindole derivatives of formula I, wherein the substituents are as defined in the specification, are particularly suitable as substance P antagonists. Several processes for preparing the compounds are also taught.

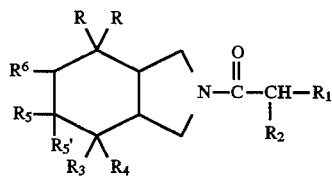

(I)

17 Claims, No Drawings

PERHYDROISOINDOLE DERIVATIVES AS SUBSTANCE P ANTAGONISTS

This application is a National Stage of PCT/FR94/00952 filed Jul. 28, 1994 and published as WO 95/04040 on Feb. 9, 1995.

The present invention relates to novel perhydroisoindole derivatives of general formula:

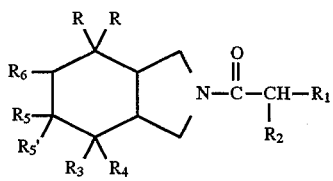

and to their salts when they exist, which antagonize the effects of substance P and are, as a result, particularly advantageous in the therapeutic fields in which this substance is known to be involved.

European Patent Application EP 429,366 has described substance P antagonists of structure:

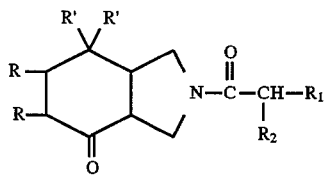

in which the symbols R are hydrogen or together form a bond, the symbols R' are optionally substituted phenyl radicals and the symbols $R_1$ and $R_2$ represent various substitutions. However, these perhydroisoindolone derivatives have proved to be mainly active in binding tests using rat brain homogenates, and display less activity in binding tests using human lymphoblast cells in culture.

U.S. Pat. No. 4,042,707 has described products derived from isoindole, of general formula:

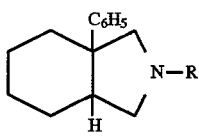

having an opiate activity. These products have no activity towards substance P.

In the general formula (I):

the symbol $R_1$ represents a phenyl radical which is optionally substituted with one or more halogen atoms or hydroxyl radicals, alkyl radicals which may be optionally substituted (with halogen atoms or amino, alkylamino or dialkylamino radicals), alkyloxy or alkylthio radicals which may be optionally substituted [with hydroxyl, amino, alkylamino or dialkylamino radicals which are optionally substituted (with phenyl, hydroxyl or amino radicals), or dialkylamino radicals in which the alkyl parts form, with the nitrogen atom to which they are attached, a 5- to 6-membered heterocycle which may contain another hetero atom chosen from oxygen, sulphur or nitrogen, optionally substituted with an alkyl, hydroxyl or hydroxyalkyl radical)], or substituted with amino, alkylamino or dialkylamino radicals in which the alkyl parts may form, with the nitrogen atom to which they are attached, a heterocycle as defined above, or represents a cyclohexadienyl, naphthyl or indenyl radical or a saturated or unsaturated mono- or polycyclic heterocyclic radical containing 5 to 9 carbon atoms and one or more hetero atoms chosen from oxygen, nitrogen or sulphur, and optionally substituted with a halogen atom or with an alkyl or alkyloxy radical, the symbol $R_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical, the symbol $R_3$ represents a phenyl radical which is optionally substituted in the 2-position with an alkyl or alkyloxy radical containing 1 or 2 carbon atoms or with a fluorine atom, or disubstituted with trifluoromethyl radicals, and the symbols $R_5$ and $R'_5$ are identical or different and one represents a hydrogen atom or a hydroxyl or alkyl radical and the other represents a hydrogen atom or an alkyl radical, and the symbol $R_4$ represents a hydroxyl radical, or alternatively the symbol $R_4$ represents a fluorine atom if the symbols $R_5$ and $R'_5$ represent a hydrogen atom or an alkyl radical, or alternatively the symbol $R_4$ forms with $R_5$ a bond, and the symbol $R_6$ represents a hydrogen atom or an alkyl, hydroxyl or hydroxyalkyl radical, and one of the symbols R represents a hydrogen atom, an alkyl radical, a hydroxyl or hydroxyalkyl radical and the other represents a hydrogen atom or an alkyl, phenyl or hydroxyalkyl radical.

It is understood that the abovementioned alkyl or acyl radicals contain (except where especially mentioned) 1 to 4 carbon atoms in a straight or branched chain.

When $R_1$ contains a halogen atom, the latter may be chosen from chlorine, bromine, fluorine or iodine.

When $R_1$ represents a saturated or unsaturated mono- or polycyclic heterocyclic radical it may, by way of example, be chosen from thienyl, furyl, pyridyl, dithiinyl, indolyl, isoindolyl, benzothienyl, thiazolyl, isothiazolyl, oxazolyl, imidazolyl, pyrrolyl, triazolyl, thiadiazolyl, quinolyl, isoquinolyl or naphthyridinyl.

When $R_1$ represents phenyl which is substituted with a chain bearing a heterocycle, the latter may be chosen from pyrrolidyl, morpholino, piperidyl, tetrahydropyridyl, piperazinyl or thiomorpholino.

Moreover, the products of general formula (I) have different stereoisomeric forms, and it is understood that the racemic forms and the stereoisomeric forms of structure:

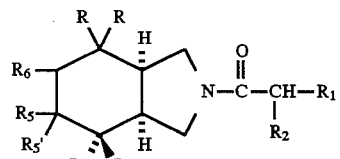

and their mixtures enter into the context of the present invention. In addition, when the symbol $R_2$ is other than a hydrogen atom, the substituted chain on the isoindole has a chiral centre, and it is understood that the (R) or (S) stereoisomeric forms and their mixtures form part of the present invention.

According to the invention, the perhydroisoindole derivatives of general formula (I) may be obtained by the action of the acid of general formula:

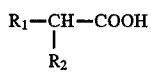  (II)

or of a reactive derivative of this acid, in which $R_1$ and $R_2$ are defined as above, on an isoindole derivative of general formula:

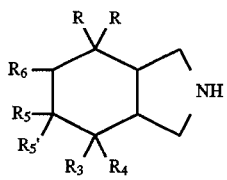  (III)

in which the symbols R, $R_3$, $R_4$, $R_5$, $R'_5$ and $R_6$ are defined as above, optionally followed by conversion of the product obtained for which $R_4$ is a hydroxyl radical and $R_5$ is a hydrogen atom or an alkyl radical to a product for which $R_4$ is a fluorine atom and $R_5$ is a hydrogen atom or an alkyl radical, or to a product for which $R_4$ and $R_5$ together form a bond.

It is understood that the amino, alkylamino or carboxyl radicals contained in $R_1$ and/or $R_2$ are preferably protected beforehand. The protection is performed by any compatible group whose installation and removal do not affect the rest of the molecule. In particular, the process is performed according to the methods described by T. W. Greene, Protective Groups in Organic Synthesis, A. Wiley—Interscience Publication (1981), or by McOmie, Protective Groups in Organic Chemistry, Plenum Press (1973).

By way of example,
the amino or alkylamino groups may be protected by methoxycarbonyl, ethoxycarbonyl, t-butoxycarbonyl, allyloxycarbonyl, vinyloxycarbonyl, trichloroethoxycarbonyl, trichloroacetyl, trifluoroacetyl, chloroacetyl, trityl, benzhydryl, benzyl, allyl, formyl or acetyl radicals or a benzyloxycarbonyl radical or its substituted derivatives;

the acidic groups may be protected by methyl, ethyl, t-butyl, benzyl, substituted benzyl or benzhydryl radicals.

In addition, when the products of general formula (II) or (III) bear hydroxyl radicals, it is preferable to protect this radical beforehand. The protection is performed according to the usual methods, for example by an acetyl, trialkylsilyl or benzyl radical, in the form of a carbonate by a radical —COORa an which Ra is an alkyl or benzyl radical, or in carbonyl or carboxyl derivative form.

It is also understood that the stereochemistry of the isoindole derivative of general formula (III) is similar to that described above for the derivatives of general formula (I).

When the condensation of a reactive derivative of the acid of general formula (II) is carried out, the procedure is advantageously performed using the acid chloride, the anhydride, a mixed anhydride or a reactive ester in which the ester residue is a succinimido radical, a 1-benzotriazolyl radical which is optionally substituted, a 4-nitrophenyl, 2,4-dinitrophenyl, pentachlorophenyl or phthalimido radical.

The reaction is generally carried out at a temperature between −40° and +40° C., in an organic solvent such as a chlorinated solvent (dichloromethane, dichloroethane or chloroform for example), a hydrocarbon (toluene for example), an ether (tetrahydrofuran or dioxane for example), an ester (ethyl acetate for example), an amide (dimethylacetamide or dimethylformamide for example), or a ketone (acetone for example) or in a mixture of these solvents, in the presence of an acid acceptor such as a nitrogen-containing organic base like, for example, pyridine, dimethylaminopyridine, N-methylmorpholine or a trialkylamine (in particular triethylamine) or such as an epoxide (propylene oxide for example). It is also possible to perform the process in the presence of a condensing agent such as a carbodiimide [for example dicyclohexylcarbodiimide or 1-(3-dimethylaminopropyl)-3-ethylcarbodiimide or N,N'-carbonyldiimdazole or 2-ethoxy-1-ethyoxycarbony-1,2-dihydroquinoline, or alternatively in an aqueous-organic medium in the presence of an alkaline condensing agent such as sodium bicarbonate.

In the alternative in which a perhydroisoindole derivative of general formula (I) has been obtained for which $R_4$ is a hydroxyl radical and $R_5$ is a hydrogen atom or an alkyl radical and in which it is desired to obtain a perhydroisoindole derivative for which $R_4$ is a fluorine atom and $R_5$ is a hydrogen atom or an alkyl radical, the procedure is performed by fluorination of the derivative obtained above.

The reaction is advantageously carried out using a fluorinating agent such as a sulphur fluoride [morpholinosulphur trifluoride, sulphur tetrafluoride (J. Org. Chem., 40, 3808 (1975)), diethylaminosulphur trifluoride (Tetrahedron, 44, 2875 (1988)) or phenylsulphur trifluoride (J. Amo Chem. Soc., 84, 3058 (1962)], such as selenium tetrafluoride (J. Am. Chem. Soc., 96, 925 (1974)) or such as tetrafluorophenylphosphorane (Tet. Let., 907 (1973)), working in an organic solvent such as a chlorinated solvent (dichloromethane or dichloroethane for example) at a temperature between −30° and 30° C. It is understood that, in the alternative in which hydroxyl radicals are present on the molecule, these radicals are protected beforehand.

In the alternative in which a perhydroisoindole derivative of general formula (I) has been obtained for which $R_4$ is a hydroxyl radical and $R_5$ is a hydrogen atom and in which it is desired to obtain a perhydroisoindole derivative for which $R_4$ and $R_5$ together form a bond, the procedure is performed by any known method for the dehydration of alcohols which does not alter the rest of the molecule. In particular, the dehydration is carried out in an acidic medium, for example by the action of a sulphonic acid (p-toluenesulphonic acid etc.), formic acid, sulphuric acid, phosphoric acid, phosphorus pentoxide or aluminium oxide or by the action of a hydrochloric acid/acetic acid or hydrobromic acid/acetic acid mixture, at a temperature between 25° C. and the reflux temperature of the reaction mixture.

According to the invention, the isoindole derivatives of general formula (I) may also be obtained by the action of an organometallic compound of general formula:

$R_3$—M  (IV)

in which $R_3$ is defined as above, and M represents lithium, a radical MgX or $CeX_2$ for which X is a halogen atom, with a perhydroisoindolone derivative of general formula:

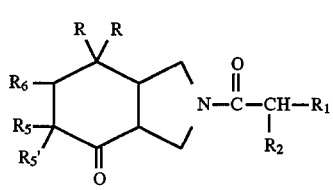  (V)

in which the symbols R, $R_1$, $R_2$, $R_5$, $R'_5$ and $R_6$ are defined as above, and for which the hydroxyl radicals are, where appropriate, preferably protected beforehand, followed by conversion, where appropriate, of the alcohol obtained of general formula (I) to a perhydroisoindole derivative for which $R_4$ is a fluorine atom and $R_5$ is a hydrogen atom or an alkyl radical or to a perhydroisoindole derivative for which $R_4$ and $R_5$ together form a bond or followed by removal, where appropriate, of the radical protecting $R_5$.

The reaction is carried out in an anhydrous medium, under the usual conditions for the reaction of organometallic compounds with a ketone, which do not affect the rest of the molecule. In particular, the procedure is performed in an ether (for example tetrahydrofuran or ethyl ether) optionally in the presence of anhydrous cerium chloride at a temperature between −78° and 30° C.

The subsequent operations for the conversion to a derivative of general formula (I) for which $R_4$ is a fluorine atom and $R_5$ is hydrogen or for which $R_4$ and $R_5$ together form a bond are carried out under the conditions described above.

According to the invention, the perhydroisoindole derivatives of general formula (I) for which one of the radicals R represents a hydroxyl radical, $R_4$ represents a hydroxyl radical and at least one of $R_5$ and $R'_5$ is a hydrogen atom, may be prepared from a perhydroisoindolone derivative of general formula:

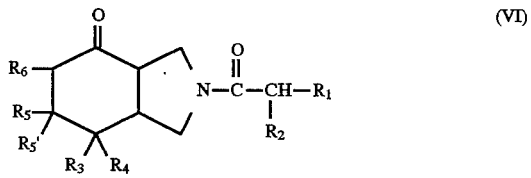

(VI)

in which $R_1$, $R_2$, $R_3$, $R_4$, $R_5$, $R'_5$ and $R_6$ are defined as above, by the action of an organometallic compound of general formula:

R—M       (VII)

in which R is an alkyl or phenyl radical or a hydroxyalkyl radical in which the hydroxyl function is protected beforehand, and M is defined as above, or by reduction in the alternative in which it is desired to obtain a derivative of general formula (I) for which the other radical R is a hydrogen atom, followed, where appropriate, by removal of the protecting radicals.

The reaction of the organometallic compound with the perhydroisoindolone derivative of general formula (VI) is carried out under analogous conditions to those described for the action of a compound of general formula (IV) on a perhydroisoindolone derivative of general formula (V).

When it is desired to obtain a perhydroisoindole derivative for which one of the R's is hydroxyl and the other is hydrogen, the reduction reaction is carried out by any known method for the reduction of ketones which does not affect the rest of the molecule; for example, the procedure is performed using sodium borohydride in an alcoholic medium (methanol for example) or using lithium aluminium hydride in an ether, at a temperature between 20° and 50° C.

According to the invention, the perhydroisoindole derivatives of general formula (I) for which the radicals $R_5$ (or $R'_5$) and $R_6$ are simultaneously hydroxyl radicals and the symbols R are other than a hydrogen atom may be prepared by the action of osmium tetroxide on a perhydroisoindole derivative of general formula:

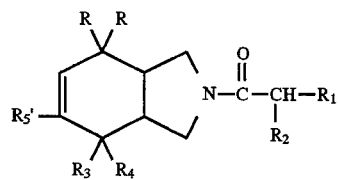

(VIII)

in which $R_1$, $R_2$, $R_3$, $R_4$, R and $R'_5$ are defined as above.

The reaction is generally carried out in pyridine at a temperature between 0° C. and the reflux temperature of the reaction mixture.

The acids of general formula (II) may be prepared according to the methods described below in the examples, according to the methods described in Patent Application EP 429,366 or by analogy with these methods.

The perhydroisoindole derivative of general formula (III) for which $R_4$ and $R_5$ together form a bond may be obtained by dehydration of the corresponding perhydroisoindole derivative for which $R_4$ is a hydroxyl radical and $R_5$ is a hydrogen atom.

The reaction is carried out under the conditions described above for the preparation of the derivatives of general formula (I) in which $R_4$ and $R_5$ together form a bond, from the corresponding perhydroisoindole derivative for which $R_4$ is a hydroxyl radical and $R_5$ is a hydrogen atom.

The isoindole derivative of general formula (III) for which $R_4$ is a fluorine atom and $R_5$ and $R'_5$ are hydrogen atoms or alkyl radicals may be prepared by fluorination of an isoindole derivative of general formula:

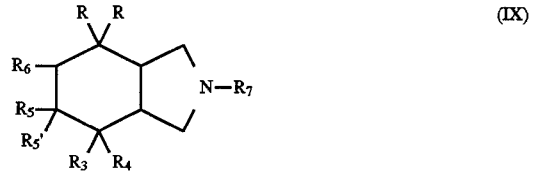

(IX)

in which R, $R_3$ and $R_6$ are defined as above, $R_7$ is a protecting radical, $R_4$ is a hydroxyl radical and $R_5$ and $R'_5$ are hydrogen atoms or alkyl radicals, followed by removal of the protecting radical $R_7$.

The protecting radical $R_7$ may be any amino-protecting group which is compatible with the reaction and whose installation and removal do not affect the rest of the molecule. By way of example, the alkyloxycarbonyl, benzyloxycarbonyl, benzyl which is optionally substituted, formyl, chloroacetyl, trichloroacetyl, trifluoroacetyl, vinyloxycarbonyl, phenoxycarbonyl, 1-chloroethoxycarbonyl or chlorocarbonyl groups may be mentioned.

The fluorination is carried out under the conditions described above for the fluorination of a derivative of general formula (I) in which $R_4$ is hydroxyl, at a temperature between −30° and +30° C. It is understood that the hydroxyl functions present in the molecule are, where appropriate, protected beforehand.

The subsequent removal of the protecting radicals is carried out according to the usual methods. In particular according to the methods described by T. W. Greene, by A. Wiley or by McOmie in the references cited above.

The perhydroisoindole derivative of general formula (III) or (IX) for which $R_4$ is a hydroxyl radical and $R_5$ is a hydrogen atom or an alkyl or hydroxyl radical may be obtained by the action of an organometallic compound of general formula (IV) on the corresponding perhydroisoindolone derivative of general formula:

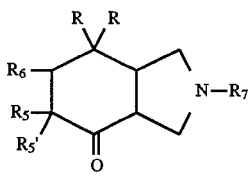

in which R, R$_5$, R'$_5$, R$_6$ and R$_7$ are defined as above, it being understood that the hydroxyl functions are, where appropriate, optionally protected, followed by freeing the radicals protecting R$_5$, R'$_5$, R$_6$ or R and optionally removing the protecting radical R$_7$ when it is desired to obtain the derivative of general formula (III).

The reaction is carried out under analogous conditions to those described for obtaining the perhydroisoindole of general formula (I) from the corresponding perhydroisoindolone of general formula (V). It is understood that, depending on the nature of the radical protecting R$_5$, R'$_5$, R$_6$ or R, this radical may be removed simultaneously with the reaction.

It is understood that, when it is desired to obtain a derivative for which R is a hydroxymethyl radical, this radical may be protected in the allyloxycarbonyl radical state on the perhydroisoindolone derivative of general formula (X). The reaction is carried out by passing via a perhydropyrano[3,4-c]pyrrol-6-one intermediate derivative which is converted by reduction and, where appropriate, by removal of the amino-protecting radical in order to obtain a derivative of general formula (III).

The perhydroisoindolone derivative of general formula (X) for which R$_5$, R'$_5$ and R$_6$ are hydrogen atoms, alkyl radicals or hydroxyl (or hydroxyalkyl) radicals which have been protected beforehand may be prepared by analogy with the method described in European Patent Application EP 429,366, or as described below in the examples.

The preparation of the perhydroisoindolone derivative of general formula (V) is carried out by analogy with the method described in European Patent Application EP 429,366, by the action of an acid of general formula (II) or of one of its reactive derivatives with a perhydroisoindolone derivative of general formula:

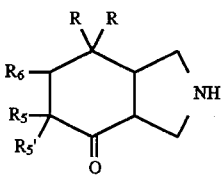

in which R, R$_3$, R'$_5$ and R$_6$ are defined as in the general formula (V) under the conditions cited in the abovementioned European Application or under the conditions cited for the action of the acids of general formula (II) on a perhydroisoindole derivative of general formula (III).

The derivatives of general formula (VI) may be obtained by the action of an acid of general formula (II) on a perhydroisoindolone of general formula:

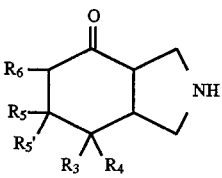

in which R$_3$, R$_4$, R$_5$, R'$_5$ and R$_6$ are defined as in the general formula (VI), by analogy with the method described for obtaining a perhydroisoindole derivative of general formula (I) from products of general formulae (II) and (III).

The perhydroisoindolone derivative of general formula (XII) may be prepared by the action of an organometallic derivative of general formula (IV) on a derivative of general formula:

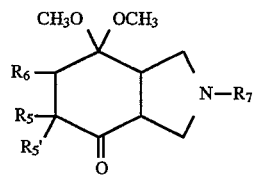

in which R$_5$, R'$_5$ and R$_6$ are defined as in the general formula (XII) and R$_7$ is a protecting radical as defined above, followed by removal of the protection from the ketone function in the 7-position and removal of the protecting radical R$_7$.

The reaction is carried out under the conditions described above for the preparation of the product of general formula (III) from a perhydroisoindolone derivative of general formula (X). The removal of the protecting radicals is carried out according to the usual methods mentioned above and/or described below in the examples.

The perhydroisoindolone derivative of general formula (XIII) may be prepared by reduction of the corresponding unsaturated derivative of general formula:

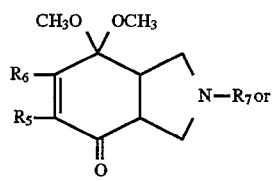

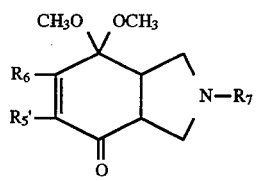

in which R$_5$, R'$_5$, R$_6$ and R$_7$ are defined as in the general formula (XIII).

The reduction is carried out by any known method which does not affect the rest of the molecule. In particular, the procedure is performed by catalytic hydrogenation in the presence of Raney nickel.

The perhydroisoindolone derivative of general formula (XIVa) or (XIVb) may be obtained from the corresponding cyclohexadienone by analogy with the method described above in European Application EP 430,771.

The starting cyclohexadienone may be obtained according to the method described in J. Org. Chem., 52, 2763 (1987).

The perhydroisoindole derivative of general formula (VIII) may be obtained by the action of an organometallic derivative of general formula (IV) on a perhydroisoindolone derivative of general formula:

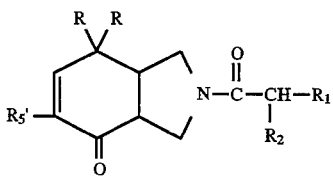

(XV)

in which $R_1$, $R_2$, $R'_5$ and R are defined as above for the general formula (VIII).

The perhydroisoindolone derivative of general formula (XV) may be prepared by analogy with the method described in European Application EP 430,771, or as described below in the examples.

The perhydroisoindole derivatives of general formulae (III), (IX), (X) and (XI) are novel products which may be defined by the structure:

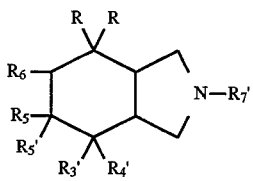

(XVI)

in which R, $R'_5$, $R_5$ and $R_6$ are defined as above, $R'_3$ and $R'_4$ are either defined as $R_3$ and $R_4$ or together form an oxo radical and $R'_7$ is either a hydrogen atom or represents a protecting radical as defined above for $R_7$.

It is well understood that the perhydroisoindole derivative of general formula (XVI) has different stereoisomeric forms and that its stereochemistry is similar to that described above for the derivatives of general formula (I).

It is understood that the perhydroisoindole derivatives of general formula (I), (III), (V), (IX), (X), (XI) or (XVI) have several stereoisomeric forms. When it is desired to obtain an enantiomer of a product of general formula (I), the separation is carried out, for example, on the derivative of general formula (I) or on the intermediate of general formula (V), (X), (XI) or (XVI) bearing an oxo radical in the 4-position. It may also be carried out on the derivative of general formula (III), (IX) or (XVI). The separation is carried out by any known method which is compatible with the molecule.

By way of example, the separation may be carried out by preparation of an optically active salt, by the action of L(+)- or D(−)-mandelic acid, or of dibenzoyltartaric or ditoluoyltartaric acid, followed by separation of the isomers by crystallization. The desired isomer is freed from its salt in a basic medium.

Another alternative may also be, where appropriate, to work directly from an enantiomer of the starting cyclohexenone.

The novel isoindole derivatives of general formula (I) may be purified, where appropriate, by physical methods such as crystallization or chromatography.

Where appropriate, the novel derivatives of general formula (I) for which the symbols $R_1$ and/or $R_2$ contain amino or alkylamino substituents, or the intermediates of general formula (III), (XI) or (XVI) for which $R'_7$ is a hydrogen atom may be converted to addition salts with acids. Examples of addition salts with pharmaceutically acceptable acids which may be mentioned are the salts formed with inorganic acids (hydrochlorides, hydrobromides, sulphates, nitrates and phosphates) or with organic acids (succinates, fumarates, tartrates, acetates, propionates, maleates, citrates, methanesulphonates, p-toluenesulphonates or isethionates, or with substitution derivatives of these compounds).

The novel isoindole derivatives of general formula (I) may also, where appropriate, when $R_2$ represents a carboxyl radical, be converted to metal salts or to addition salts with a nitrogen-containing base, according to the methods known per se. These salts may be obtained by the action of a metal base (for example alkali metal or alkaline-earth metal base), ammonia or an amine on a product according to the invention, in a suitable solvent such as an alcohol, an ether or water, or by exchange reaction with a salt of an organic acid. The salt formed precipitates after optional concentration of the solution, and it is separated out by filtration, decantation or freeze-drying. Examples of pharmaceutically acceptable salts which may be mentioned are salts with alkali metals (sodium, potassium or lithium) or with alkaline-earth metals (magnesium or calcium), the ammonium salt, salts of nitrogen-containing bases (ethanolamine, diethanolamine, trimethylamine, triethylamine, methylamine, propylamine, diisopropylamine, N,N-dimethylethanolamine, benzylamine, dicyclohexylamine, N-benzyl-β-phenethylamine, N,N'-dibenzylethylenediamine, diphenylenediamine, benzhydrylamine, quinine, choline, arginine, lysine, leucine or dibenzylamine).

The novel isoindole derivatives according to the present invention which antagonize the effects of substance P may find an application in the fields of analgesia, inflammation, asthma, allergies, on the central nervous system, on the cardiovascular system, as antispasmodic agents, as antiemetic agents, or on the immune system, as well as in the field of stimulation of lachrymal secretions.

In fact, the products according to the invention display an affinity for substance P receptors at concentrations between 5 and 1000 nM according to the techniques adapted from D. G. Payan et al., J. of Immunology, 133(6), 3260–5 (1984): Stereospecific receptors for substance P on cultured human IM-9 lymphoblasts, and from McPherson et al., J. Pharmacol. Meth., 14, 213 (1985): Analysis of radioligand binding experiments.

It has in addition been demonstrated that this is an antagonistic effect on substance P, using various products. In the technique described by S. Rosell et al., Substance P, Ed. by U. S. Von Euler and B. Pernow, Raven Press, New York (1977), pages 83 to 88, the products studied display an antagonism of the contractions of guinea pig ileum induced by substance P or contractions of guinea pig ileum induced by septide, at concentrations of 1 to 1000 nM.

Substance P is known to be involved in a certain number of pathological fields:

Agonists and antagonists of substance P, A. S. Dutta, Drugs of the future, 12 (8), 782 (1987);

Substance P and pain: an updating, J. L. Henry, TINS, 3(4), 97 (1980);

Substance P in inflammatory reactions and pain, S. Rosell, Actual. Chim. Ther., 12ème série, 249 (1985);

Effects of Neuropeptides on Production of Inflammatory Cytokines by Human Monocytes, M. Lotz et coll., Science, 241, 1218 (1988);

Neuropeptides and the pathogenesis of allergy, Allergy, 42, 1 to 11 (1987);

Substance P in Human Essential Hypertension, J. Cardiovascular Pharmacology, 10 (suppl. 12), 5172 (1987).

The study of certain isoindole derivatives of general formula (I) in the technique of A. Saria et al., Arch. Pharmacol., 324, 212–218 (1983) adapted to the guinea pig has made it possible to demonstrate an inhibitory effect of the increase of the capillary permeability brought about by septide (substance P agonist), which bears evidence of an anti-inflammatory activity:

| Product studied | ED$_{50}$ |
| --- | --- |
| Example 1 | 0.07 mg/kg i.v. |
|  | 3 to 10 mg/kg p.o. |

The injection of substance P into animals induces a bronchospasm. The bronchoconstriction induced in vivo in guinea pigs by the injection of substance P or of a selective substance P agonist: septide, is studied according to the technique of H. Konzett and R. Rosseler, Archiv. Exp. Path. Pharmak., 195, 71–74 (1940). This bronchoconstriction is inhibited by the injection of a product according to the invention, which bears evidence of an anti-asthmatic activity.

Moreover, the products according to the invention are studied in the formaldehyde pain test in guinea pigs. The ED$_{50}$ of the product is thus determined.

Finally, the isoindole derivatives according to the present invention display no toxicity; they proved to be non-toxic in mice at the dose of 40 mg/kg via the subcutaneous route.

The present invention also relates to the synergizing combination consisting of at least one antagonist of NK1 receptors of general formula (I) and at least one antagonist of NK2 receptors.

The effects of neurokinin A are mainly mediated via the NK2 receptors. Neurokinin A is involved in numerous pathologies, such as the transmission of pain, arthritis, asthma, inflammatory phenomena, psychosis, blood pressure disorders, vesical disorders, cystitis, etc.

NK2-receptor antagonists (antagonists of the effects of neurokinin A) are known and described in particular in Patent Applications EP 428,434, EP 474,561, EP 512,901, EP 515,240, FR 2,678,267, WO 92/19254 and WO 93/14084.

NK2-receptor antagonists may in particular be, in a non-limiting manner, derivatives of the arylalkylamine class, the α-substituted polypeptide class or the class of piperidine derivatives, etc.

By way of example, NK2-receptor antagonists of the arylalkylamine class may be products of general formula:

$$Y\underset{\diagdown\diagup}{\diagup\diagdown}N-(CH_2)_m-\underset{\underset{Ar}{|}}{\overset{\overset{R'}{|}}{C}}-(CH_2)_p-\overset{\overset{R}{|}}{N}-T-(CH_2)_q-Z \quad (XVII)$$

in which:

1) Y is a group >N—CXX'—Ar', >CH—CXX'—Ar' or >C=CX—Ar' for which X is H and X' is H or OH or X and X' together form an oxo radical or a dialkylaminoalkyloxyimino radical for which the alkyl parts contain 1 to 4 carbon atoms and the alkyloxy part contains 2 or 3 carbon atoms, Ar and Ar' are independently thienyl, phenyl which is optionally mono- or polysubstituted (by halogen, alkyl or alkoxy (1 to 3 carbon atoms), trifluoromethyl, hydroxyl or methylenedioxy) or imidazolyl, or alternatively Ar may be benzothienyl or naphthyl which are optionally substituted with halogen, biphenyl, or indolyl which may bear a benzyl group on the nitrogen atom, R' is a hydrogen atom, an alkyl radical (1 to 4 carbon atoms), an alkyl radical (2 or 3 carbon atoms) which is substituted (with piperidino, 4-benzylpiperidino or dialkylamino in which the alkyl parts, contain 1 to 4 carbon atoms), R and T are defined as for the general formula (VI) and Z is H, straight or branched alkyl (1 to 6 carbon atoms), phenylalkyl in which the alkyl part contains 1 to 3 carbon atoms and which is optionally mono- or polysubstituted on the phenyl by halogen, OH, alkyl or alkyloxy (1 to 4 carbon atoms), pyridylalkyl or naphthylalkyl or pyridylthioalkyl or 2-(1-methyl) imidazolylthioalkyl in which the alkyl part contains 1 to 3 carbon atoms, styryl, 1-oxo-3-phenylindan-2-yl, or an unsubstituted, mono- or polysubstituted aromatic or heteroaromatic group, and m is an integer from 1 to 3, p is equal to 1 and q is equal to 0, or alternatively 2) Y is a group >N—Ar' for which Ar' is a phenyl radical which may be substituted one or more times (with halogen, OH, alkyloxy or alkyl (1 to 4 carbon atoms) or trifluoromethyl), or a pyrimidinyl or pyridyl radical, a group >N-cycloalkyl (3 to 7 carbon atoms), or alternatively a group >CH—(CH$_2$)$_x$—Ar' for which Ar' is defined as above with the exception of representing pyrimidinyl, or represents thienyl, X is OH, alkyloxy (1 to 4 carbon atoms), hydroxyalkyl or acyloxy in which the alkyl part contains 1 to 3 carbon atoms, phenacyloxy, carboxyl, carbalkyloxy (1 to 4 carbon atoms), cyano, aminoalkylene (1 to 3 carbon atoms), amino, alkylamino or dialkylamino in which the alkyl parts contain 1 to 4 carbon atoms, acylamino (2 to 7 carbon atoms), acylaminoalkyl in which the alkyl parts contain 1 to 3 carbon atoms, acyl, —SH, alkylthio in which the alkyl part contains 1 to 4 carbon atoms and x is 0 or 1, or alternatively a group =C—(CH$_2$)$_x$—Ar' in which Ar' is defined as above, T is defined as in 1), and Z s defined as in 1) with the exception of representing 2-(1-methyl) imidazolylthioalkyl or 1-oxo-3-phenylindan-2-yl, or represents phenylalkyl which is substituted with trifluoromethyl or naphthylalkyl in which the alkyl part contains 1 to 3 carbon atoms and is optionally substituted on the naphthyl ring with a halogen atom or with a trifluoromethyl, OH, alkyl or alkyloxy (1 to 4 carbon atoms) radical, Ar is thienyl, phenyl which is optionally mono- or polysubstituted (with halogen, alkyl or alkyloxy (1 to 4 carbon atoms) or trifluoromethyl) or benzothienyl, naphthyl or indolyl which may bear an alkyl group (1 to 3 carbon atoms) on the nitrogen atom, R' is a hydrogen atom, R is a hydrogen atom or an alkyl radical (1 to 6 carbon atoms), and m is an integer equal to 2 or 3, p is equal to 1 and q is equal to 0, or alternatively 3) Y is a group >N—Ar' or >N—CH$_2$—Ar' for which Ar' is defined as above in 2), or alternatively a group >CX—(CH$_2$)$_x$—Ar' as defined above, X being OH, alkyloxy, acyloxy or carbalkyloxy (1 to 4 carbon atoms), carboxyl, cyano, amino which is optionally mono- or disubstituted (with alkyl, hydroxyalkyl or acyl (1 to 4 carbon atoms)), pyrrolidino, piperidino or morpholino, —SH or alkylthio in which the alkyl part contains 1 to 4 carbon atoms and x is 0 is 1, or alternatively a group =C—(CH$_2$)$_x$—Ar' in which Ar' is defined as above, Ar is defined as above in 2) with the exception of representing a substituted indolyl radical, R and R' together form a chain

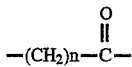

in which Q is an oxygen atom or 2 hydrogen atoms, T is —CO— or —CH$_2$— and

Z is phenyl or naphthyl which are optionally mono- or polysubstituted with halogen, trifluoromethyl, OH or alkyl (1 to 4 carbons), or with alkyloxy (1 to 4 carbons) when Z is phenyl, pyridyl, thienyl, indolyl, quinolyl, benzothienyl or imidazolyl, or an unsubstituted, mono- or polysubstituted aromatic or heteroaromatic group, or when T is CO, —(CH$_2$)$_q$—Z may be benzyl in which the methyl radical is substituted with OH, alkyl or alkyloxy (1 to 4 carbons), and m is an integer equal to 2 to 3, p is equal to 1 to 2, n is equal to 0 to 3 and q is equal to 0 to 3, it being understood that if p=2: n=1 and Q represents 2H; or alternatively 4) Y is a group Ar'—X— for which Ar' represents thienyl, phenyl which is optionally mono- or polysubstituted (with halogen, alkyl or alkyloxyl (1 to 3 carbons), trifluoromethyl, hydroxyl or methylenedioxy), pyridyl or imidazolyl which is optionally substituted with an alkyl radical, and X is an oxygen or sulphur atom or a sulphonyl, sulphinyl, —NH—, >N—CO—Alk, >N—Alk or >N—Alk—NX$_1$X$_2$ radical for which Alk is alkyl or alkylene (1 to 3 carbons) and X$_1$ and X$_2$ are H, alkyl (1 to 3 carbons) or form, with the nitrogen atom, a piperidine, pyrrolidine or morpholine ring, R' is a hydrogen atom, an alkyl radical (1 to 4 carbons) or an aminoalkyl radical in which the alkyl part, in a straight chain, contains 2 or 3 carbon atoms and the amino group may be dialkylamino in which the alkyl parts contain 1 to 4 carbon atoms, piperidino or 4-benzylpiperidino radical, Ar, R and T are defined as in 1), Z is defined as above 1) or represents α-hydroxybenzyl or α-alkoxybenzyl in which the alkyl part contains 1 to 3 carbon atoms, and m, p and q are defined as above in 2), or alternatively 5) Y is a group >CX—(CH$_2$)$_x$—Ar' for which Ar' is thienyl, phenyl which is optionally mono- or polysubstituted (with halogen, alkyl or alkyloxy (1 to 4 carbons), trifluoromethyl or hydroxyl) or pyridyl, x is 0 or 1 and X is —NH—CO—alkyl gift the alkyl part contains 1 to 6 carbon atoms, m is 2 or 3, p is 1 and q is equal to 0

At, T and Z are defined as in 2),

R' is H and R is H or alkyl; and among these products a specific antagonist of the NK2 receptors, is described more particularly by X. Emonds-Alt et al., Life Science, 50, PL100 to PL106 (1992).

By way of example, NK2-receptor antagonists of the α-substituted polypeptide class, may be products of general formula:

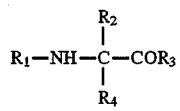

in which

R$_1$ is a hydrogen atom or an N-terminal group consisting of 0 to 4 amino acids, R$_2$ is an amino acid side chain except for glycine, R$_3$ is a C-terminal group consisting of 0 to 4 amino acids, a radical OH or OR in which R is a straight or branched alkyl radical or a cycloalkyl radical containing 1 to 6 carbon atoms, R$_4$ is an amino acid side chain except for glycine, or a radical —CH=CH$_2$, —CH≡CH, —CH$_2$—CH=CH$_2$, —CH$_2$—CH=CH, —CH$_2$—Ar, —CH$_2$—OR, —CH$_2$—OAr, —(CH$_2$)$_n$CO$_2$R or —CH$_2$—NR$_5$R$_6$, n being an integer from 0 to 3, R being H or a lower alkyl radical and Ar being a substituted or unsubstituted mono- or polycyclic aromatic or hydroaromatic carbocycle or heterocycle, it being understood that R$_1$ and R$_3$ cannot comprise more than 4 amino acid residues in total.

By way of example, NK2-receptor antagonists of the piperidine derivatives class, may be products of general formula:

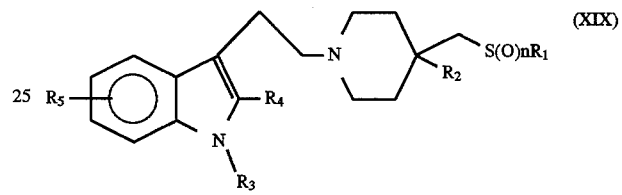

in which R$_1$ is phenyl which is optionally substituted with 1 or 2 alkyl, alkyloxy, CF$_3$ or halogen [lacuna], R$_2$ is H, OH or alkyl, R$_3$ is H or alkyl, R$_4$ is H, alkyl or alkyloxy, and R$_5$ is H, alkyl, CF$_3$, CN or halogen and n is 0 to 2, the alkyl radicals having 1 to 4 carbons; and among these products 1-[2-(5-fluoro-1H-indol-3-yl)ethyl]-4-[(phenylsulphinyl)methyl]-4-piperidinol may more especially be mentioned.

Of particular value are the perhydroisoindole derivatives of general formula (I) for which the symbol R$_1$ represents a phenyl radical which is optionally substituted with a hydroxyl, alkyloxy or dialkylamino radical, or a saturated or unsaturated mono- or polycyclic heterocyclic radical containing 5 to 9 carbon atoms and one or more hetero atoms chosen from oxygens nitrogen or sulphur, the symbol R$_2$ represents a hydrogen atom or an alkyl radical, the symbol R$_3$ represents a phenyl radical which is optionally substituted in the 2-position with an alkyloxy radical containing 1 or 2 carbon atoms or with a fluorine atom, or is disubstituted with trifluoromethyl radicals, the symbols R$_5$ and R'$_5$ are identical or different and one represents a hydrogen atom or a hydroxyl or alkyl radical and the other represents a hydrogen atom or an alkyl radical, the symbol R$_4$ represents a hydroxyl radical and the symbol R$_6$ represents a hydrogen atom or an alkyl, hydroxyl or hydroxyalkyl radical, and one of the symbols R represents a hydrogen atom, an alkyl radical, a hydroxyl or hydroxyalkyl radical and the other a hydrogen atom or an alkyl or phenyl radical.

Among these products which are especially active are the following perhydroisoindole derivatives:

7,7-dimethyl-4-(2-methoxyphenyl)-2-[(S)-2-(2-methoxyphenyl)propionyl]-4,5-perhydroisoindolediol 4-(2-methoxyphenyl)-5-[2-(S)-(2-methoxyphenyl)propionyl[-5-methyl-4-perhydroisoindolol 2-[2-(S)-(2-hydroxyphenyl)propionyl]-4-(2-methoxyphenyl)-6-methyl-4-perhydroisoindolol 7-(hydroxymethyl)-4-(2-methyoxyphenyl)-2-(S)-[2-(2-methoxyphenyl)propionyl]-7-methyl-4-perhydroisoindolol 7-(hydroxymethyl)-2-(3-indolylacetyl)-4-(2-methoxyphenyl)-7-methyl-4-perhydroisoindolol.

The examples which follows, given without any limitation being implied, illustrate the present invention.

In the examples which follow, it is understood that, except where especially mentioned, the proton NMR spectra where obtained at 250 MHz in dimethyl sulphoxide; the chemical shifts are exposed in ppm.

EXAMPLE 1

To a solution of 1.54 g of (3aRS,4RS,6SR,7aSR)-4-(2-methoxyphenyl)-6-methyl-4-perhydroisoindolol in 150 cm$^3$ of dichloromethane is added 1.0 cm$^3$ of triethylamine. The reaction is mixture is cooled to 5° C. and 1.08 g of (S)-2(2-methoxyphenyl)propionic acid, 0.10 g of 1-hydroxybenzotriazole monohydrate and 1.26 g of 1-(3-dimethylaminopropyl)-3-ethylcarbodiimide hydrochloride are added. The reaction mixture is maintained for 1 hour at 5° C. and for 16 hours at 20° C. and is then washed twice with 100 cm$^3$ of water, dried over magnesium sulphate, filtered and concentrated to dryness under reduced pressure (2.7 kPa). The residue is chromatographed on a column of silica gel (0.060–0.200 mm, diameter 4 cm, height 70 cm), eluting under a pressure of 0.7 bar with a mixture of ethyl acetate and cyclohexane [by volume: 20/80 (2 dm$^3$) then 30/70 (2 dm$^3$) then 40/60 (2 dm$^3$) and collecting 60 cm$^3$ fractions. Fractions 57 to 72 are concentrated and, after drying at 40° C. at 15 Pa, 0.90 g of (3aR*,4R*,6S*,7aS*)-4-(2-methoxyphenyl)-2-[2-(S)-(2-methoxyphenyl)propionyl]-6-methyl-4-perhydroisoindolol is obtained in the form of a white solid.

Proton NMR spectrum (250 MHz, DMSO d$_6$+a few drops of CD$_3$COOD, at a temperature of 383° K., δ in ppm and J in Hz): 0.9 (d, J=6.5 Hz, 3H); 1.25 (broad d, J=7 Hz, 3H) 2.8 (t, J=8 Hz, 1H); 3.6 (broad s, 3H); 3.8 (broad s, 3H); 4.1 (broad s, 1H); 6.9–7.6 (m, 8H)

IR spectrum (KBr, cm$^{-1}$): 3410, 3070, 3000–2850, 2835, 1635, 1600, 1585, 1495, 1450, 1240, 1060, 1030, 755.

2-(S)-(2-Methoxyphenyl)propionic acid may be prepared according to the method described in Patent Application EP 429,366.

(3aRS,4RS,6SR,7aSR)-4-(2-Methoxyphenyl)-6-methyl-4-perhydroisoindolol may be obtained in the following way:

To 3.5 g of (3aRS,4RS,6SR,7aSR)-2-benzyl-4-(2-methoxphenyl)-6-methyl-4-perhydroisoindolol are added, at 20° C. and under a nitrogen atmosphere, 1.2 g of 10% palladium on charcoal and 75 cm$^3$ of ethanol. After heating at 50° C. and sparging with hydrogen for two hours, the reaction mixture is cooled to room temperature and flushed using a stream of nitrogen, filtered and concentrated under reduced pressure (2.7 kPa). 2.1 g of (3aRS,,4RS,6SR,7aSR)-4-(2-methoxyphenyl)-6-methyl-4-perhydroisoindolol are obtained in the form of a white solid. M.p.=164° C.

Proton NMR spectrum (250 MHz, CDCl$_3$, δ in ppm and J in Hz): 0.60 (d, J=6.5 Hz, 3H); 1.8 (m, 1H); 2.25 (m, 1H); 2.6 (t, J=9 Hz, 1H); 2.8 (t, J=9.5 Hz, 1H); 3.5 (s, 3H); 6.60 (m, 2H); 6.88 (broad t, J=8 Hz, 1H); 7.5 (broad d, J=8 Hz, 1H)

(3aRS,4RS,6SR,7aSR)-2-Benzyl-4-(2-methoxphenyl)-6-methyl-4-perhydroisoindolol may be obtained in the following way:

135 cm$^3$ of 1.6M n-butyllithium solution in hexane are added to 31.3 cm$^3$ of anisole diluted in 400 cm$^3$ of t-butyl methyl ether and 33 cm$^3$ of tetramethylethylenediamine, while maintaining the temperature below 30° C. After one hour at 20° C., the reaction mixture is cooled to −72° C. and 24 g of (3aRS,6SR,7aSR)-2-benzyl-6-methyl-4-perhydroisoindolone dissolved in 200 cm$^3$ of tetrahydrofuran are added at this temperature over thirty minutes. After stirring for thirty minutes, 200 cm$^3$ of aqueous 26% ammonium chloride solution are poured in over thirty minutes and the reaction mixture is warmed to room temperature and decanted. The organic phase is washed with water (3 times 150 cm$^3$) and then with saturated sodium chloride solution (150 cm$^3$), dried over magnesium sulphate, filtered and concentrated under reduced pressure (2.7 kPa). The residue obtained is chromatographed on a column of silica gel (0.060–0.200 mm, diameter 6 cm, height 55 cm), eluting under a pressure of 0.7 bar with a mixture of ethyl acetate and cyclohexane [by volume: 30/70 (3 dm$^3$) then 50/50 (2 dm$^3$) and 100/0 (3 dm$^3$)] and collecting 200 cm$^3$ fractions. Fractions 9 to 26 are combined, concentrated to dryness under reduced pressure (2.7 kPa) and crystallized in isopropyl ether. 20.5 g of (3aRS,4RS,6SR,7aSR)-2-benzyl-4-(2methoxyphenyl)-6-methyl-4-perhydroisoindolol are obtained in the form of white crystals, m.p.=120° C.

Proton NMR spectrum (250 MHz, CDCl$_3$, δ in ppm and J in Hz): 0.9 (d, J=6.5 Hz, 3H); 2.15 (m, 1H); 3.58 and 3.80 (AB, J=13 Hz, 2H); 3.85 (s, 3H); 6.85 (dd, J=7.5 and 1.5 Hz, 1H); 7.0 (ddd, J=7.5 and 1.5 Hz, 1H); 7.3 (m, 5H); 8.0 (dd, J=7.5 and 2 Hz, 1H)

IR spectrum (KBr, cm$^{-1}$): 3350–3150, 3100–3000, 3000–2850, 2835, 2815, 2735, 1595, 1580, 1495, 1485, 1450, 1235, 1035.

(3aRS,6SR,7aSR)-2-Benzyl-6-methyl-4-perhydroisoindolone may be obtained in the following way:

To a solution of 15.9 g of 5-methyl-cyclohex-2-enone and 50 cm$^3$ of N-butoxymethyl-N-trimethylsilylmethylbenzylamine in 200 cm$^3$ of dichloromethane are added 10 drops of trifluoroacetic acid. The reaction mixture reaches reflux after fifteen minutes and then returns slowly (2 hours) to 20° C. 10 g of potassium carbonate are added to the mixture which is stirred for 30 minutes, filtered and concentrated under reduced pressure (2.7 kPa). The residue obtained is chromatographed on a column of silica gel (0.060–0.200 mm, diameter 6 cm, height 50 cm), eluting under a pressure of 0.7 bar with a mixture of ethyl acetate and cyclohexane [by volume: 40/60 (4 dm$^3$) then 60/40 (4 dm$^3$) and 100/0 (2 dm$^3$)] and collecting 250 cm$^3$ fractions. Fractions 9 to 42 are combined and concentrated to dryness under reduced pressure (2.7 kPa), and 24 g of (3aRS,6SR,7aSR)-2-benzyl-6-methyl-4-perhydroisoindolone are obtained in the form of an oil.

Proton NMR spectrum (250 MHz, CDCl$_3$, δ in ppm and J in Hz): 1.0 (d, J=6.5 Hz, 3H); 1.55 (ddd, J=14, 11 and 6 Hz, 1H); 1.75 (ddd, J=14, 6 and 3 Hz, 1H); 2.1 (m, 1H); 3.6 (s, 2H); 7.3 (bm, 5H)

N-Butoxymethyl-N-trimethylylmethybenzylamine may be prepared according to the method of Y. Terao et al., Chem. Pharm. Bull., 33, 2762 (1985).

5-Methylcyclohex-2-enone may be prepared according to the method described by P. L. Fuchs and A. K. Musser, J. Org. Chem., 47, 3121 (1982).

EXAMPLE 2

In an identical manner to Example 1, 0.78 g of (3aRS, 4RS,6SR,7aSR)-4-(2-methoxyphenyl)-6-methyl-4-perhydroisondolol and 0.52 g of (2-methoxyphenyl)acetic acid are used. After chromatography on a column of silica gel (0.060–0.200 mm, diameter 3.5 cm, height 40 cm), eluting under a pressure of 0.7 bar with a mixture of dichloromethane and methanol [94/6 by volume] and collecting 45 cm³ fractions, fractions 8 to 15 are concentrated and, after drying at 40° C. at 15 Pa, 1.0 g of (3aRS,4RS, 6SR,7aSR)-4-(2-methoxphenyl)-2-[(2-methoxphenyl) acetyl]-6-methyl-4-perhydroisoindolol is obtained in the form of a white solid, m.p.=186° C.

Proton NMR spectrum (250 MHz, DMSO d₆+a few drops of CD₃COOD, at a temperature of 383° K., δ in ppm and J in Hz): 0.9 (d, J=6.5 Hz, 3H); 2.2 (m, 1H); 2.6 (broad m, 1H); 2.9 (t, J=7 Hz, 1H); 3.75 (s, 3H); 3.85 (s, 3H); 6.90 (m, 4H); 7.2 (m, 3H); 7.6 (dd, J=8 and 1.5 Hz, 1H).

IR spectrum (KBr, cm⁻¹): 3410, 3100–3000, 3000–2850, 2845, 2800–2300, 1635, 1595, 1495, 1460, 1235, 1115, 1025, 760.

EXAMPLE 3

To a solution of 0.78 g of (3aRS,4RS,6SR,7aSR)-4-(2-methoxyphenyl)-6-methyl-4-perhydroisoindolol in 80 cm³ of dichloromethane is added 0.5 cm³ of triethylamine. The reaction mixture is cooled to 5° C. and 0.54 g of (2-dimethylaminophenyl)acetic acid, 0.05 g of 1-hydroxybenzotriazole monohydrate and 0.63 g of 1-(3-dimethylaminopropyl)-3-ethylcarbodiimide hydrochloride are added. The reaction mixture is maintained for 1 hour at 5° C. and for 16 hours at 20° C. and is then washed twice with 100 cm³ of water, dried over magnesium sulphate, filtered and concentrated under reduced pressure (2.7 kPa). The residue is chromatographed on a column of silica gel (0.060–0.200 mm, diameter 4 cm, height 50 cm), eluting under a pressure of 0.7 bar with a mixture of dichloromethane and methanol [97.5/2.5 by volume] and collecting 65 cm³ fractions. Fractions 17 to 23 are concentrated and, after drying at 40° C. at 15 Pa, 0.90 g of (3aRS,4RS, 6SR,7aSR)-4-(2-methoxyphenyl)-2-[(2-dimethylaminophenyl)acetyl]-6-methyl-4-perhydroisoindolol is obtained in the form of a white powder which is dissolved in 50 cm³ of dioxane. 3 cm³ of 5M hydrochloric acid solution in dioxane are added and, after 1 hour at room temperature, the solution is concentrated under reduced pressure (2.7 kPa), triturated in isopropyl ether, filtered and dried at 40° C. at 15 Pa. 1.0 g of (3aRS,4RS, 6SR,7aSR)-4-(2-methoxyphenyl)-2-[(2-dimethylaminophenyl)acetyl]-6-methyl-4-perhydroisoindolol hydrochloride is obtained.

Proton NMR spectrum (250 MHz, DMSO d₆+a few drops of CD₃COOD, at a temperature of 413° K., δ in ppm and J in Hz): 0.95 (d, J=7.5 Hz, 3H); 1.40 (ddd, J=17.51, 13.5 and 7.5 Hz, 1H); 1.7 (m, 1H); 1,85 (d, J=17.5 Hz, 1H); 2.05 (m, 1H); 2.2 (m, 1H); 2.6 (m, 1H); 3.1 (s, 6H); 3.6 (s, 2H); 3.87 (s, 3H); 6.9–7.7 (m, 8H)

IR spectrum (KBr, cm⁻¹): 3410, 3100–3000, 3000–2850, 2845, 2800–2300, 1635, 1595, 1495, 1460, 1235, 1115, 1025, 760.

2-Dimethylaminophenylacetic acid may be prepared according to the method described in Patent Application EP 429,366.

EXAMPLE 4

In an identical manner to Example 1, 0.78 g of (3aRS, 4RS,6SR,7aSR)-4-(2-methoxyphenyl)-6-methyl-4 perhydroisoindolol and 0.52 g of 3-indoleacetic acid are used. After chromatography on a column of silica gel (0.060–0.200 mm, diameter 3.5 cm, height 40 cm), eluting under a pressure of 0.7 bar with a mixture of dichloromethane and methanol [94/6 by volume] and collecting 45 cm³ fractions, fractions 10 to 16 are concentrated to dryness and, after drying at 40° C. at 15 Pa, 1.0 g of (3aRS,4RS, 6SR,7aSR)-2-(3-indolylacetyl)-4-(2-methoxyphenyl)-6-methyl-4-perhydroisoindolol is obtained in the form of a white solid.

Proton NMR spectrum (250 MHz, DMSO d₆+a few drops of CD₃COOD, at a temperature of 383° K., δ in ppm and J in Hz): 0.9 (d, J=6.5 Hz, 3H); 2.2 (m, 1H); 2.6 (m, 1H); 2.88 (t, J=7 Hz, 1H); 3.65 (s, 2H); 3.85 (s, 3H); 6.9–7.6 (m, 9H).

IR spectrum (KBr, cm⁻¹): 3410, 3260, 3100–3000, 3000–2850, 2835, 1625, 1585, 1415, 1450, 1235, 1105, 1025, 755, 745.

EXAMPLE 5

By working according to the experimental procedure of Example 6 below, from 1 g of (3aRS,4RS,7aSR)-4-(2-methoxyphenyl)-4perhydroisoiindolol and 0.87 g of 2-(S)-(2-methoxyphenyl)propionic acid, and after purification on a column of silica gel (particle size 0.04–0.06 mm, diameter 3.2 cm, height 18 cm), 0.19 g of (3aR*,4R*,7aS*)-4-(2-methoxyphenyl)-2-[2-(S)-(2-methoxyphenyl)propionyl]-4-perhydroisoindolol is obtained in the form of a white foam.

Proton NMR spectrum (DMSO d₆):

6.5, 1H, H at 3); 3.78 (bs, 3H, OCH₃); 3.85 (s, 3H, OCH₃); 4.17 (bq, J=7.5, CH—CH₃); 6.9 to 7.25 (m, 8H) aromatic).

IR spectrum (KBr—characteristics bands in cm⁻¹):

3425, 3070, 3000–2850, 2835, 1635, 1595, 1580, 1495, 1450, 1245, 1060, 1035, 755.

(3aRS,4RS,7aSR)-4-(2-Methoxyphenyl)-4-perhydroisoindolol may be prepared in the following way:

A mixture of 16 g of (3aRS,4RS,7aSR)-2-benzyl-4-(2-methoxyphenyl)-4-perhydroisoindolol and 200 cm³ of anhydrous ethanol is heated at 60° C. with stirring; 2 g of 20% palladium hydroxide on charcoal are added and the reaction mixture is then hydrogenated, with stirring, at a temperature of 60° C. and at atmospheric pressure. After reaction for 6 hours the reaction mixture is filtered and then concentrated to dryness under reduced pressure (2.7 kPa). 5.72 g of (3aRS,4RS,7aSR)-4-(2-methoxyphenyl)-4-perhydroisoindolol are obtained in the form of a cream-coloured foam.

(3aRS,4RS,7 aSR)-2-Benzyl-4-(2-methoxyphenyl)-4-perhydroisoindolol may be prepared in the following way:

To a suspension of 55.63 g of 2-methoxyphenylmagnesium bromide in 250 cm³ of tetrahydrofuran is added dropwise, at room temperature and with stirring, a solution of 20.16 g of (3aRS,7aSR)-2-Benzyl-4-perhydroisoindolone in 250 cm³ of tetrahydrofuran. The reaction mixture is stirred at room temperature for 18 hours, treated with 300 cm³ of saturated aqueous ammonium chloride solution, taken up in 200 cm³ of ethyl ether and washed with 300 cm³ of saturated aqueous sodium chloride solution. The organic phase is separated out after settling has taken place, dried over magnesium sulphate, filtered and concentrated to dryness under reduced pressure (2.7 kPa). The residue is chromatographed on a column of silica gel (particle size 0.04–0.06 mm, diameter 8.8 cm, height 41 cm), eluting under a pressure of 0.5 bar of nitrogen with a mixture of cyclohexane and ethyl acetate (80/20 by volume) and collecting 1000 cm³fractions. Fractions 4 to 27 are combined and then concentrated to dryness under reduced pressure (2.5 kPa). 24.96 g of (3aRS,4RS,7aSR)-2-benzyl-4-(2-methoxyphenyl)-4-perhydroisoindolol are obtained in the form of white crystals melting at 106° C.

(3aRS,7aSR)-2-Benzyl-4-perhydroisoindolone may be prepared in the following way:

To a solution of 20 g of 2-cyclohexenone and 69 cm³ of N-butoxymethyl-N-trimethylbenzylamine in 250 cm³ of dichloromethane are added, at a temperature of 10° C., 5 drops of trifluoroacetic acid. The reaction mixture is stirred at this temperature for 3 hours, then potassium carbonate is added and the solution is filtered through a sinter funnel and concentrated to dryness under reduced pressure (2.7 kPa). The residue is chromatographed on a column of silica gel (particle size 0.04–0.06 mm, diameter 8.8 cm, height 38 cm), eluting under a pressure of 0.5 bar of nitrogen with a mixture of cyclohexane and ethyl acetate (75/25 by volume) and collecting 1000 cm³ fractions. Fractions 4 to 26 are combined and concentrated to dryness under reduced pressure (2.7 kPa). 28.23 g of (3aRS,7aSR)-2-benzyl-4-perhydroisoindolone are obtained in the form of a yellow oil.

N-Butoxymethyl-N-trimethylsilymethylbenzylamine may be prepared according to the method of Y. Tarao et al., Chem. Pharm. Bull., 33, 2762, (1985).

EXAMPLE 6

To a solution of 1.5 g of (3aRS,4RS,7aSR)-4-(2-methoxyphenyl)-4-perhydroisoindolol and 1.27 g of 3-indoleacetic acid in 40 cm³ of dichloromethane, cooled to 0° C., are added 0.08 g of 1-hydroxybenzotriazole and 1.4 g of 1-(3-dimethylaminopropyl)-3-ethylcarbodiimide hydrochloride. The mixture is stirred for 18 hours at room temperature and the organic phase is then washed with twice 80 cm³ of water and then with 80 cm³ of saturated aqueous sodium chloride solution, dried over magnesium sulphate and concentrated to dryness under reduced pressure (2.7 kPa). The residue is chromatographed on a column of silica gel (particle size 0.04–0.06 mm, diameter 4 cm, height 40 cm), eluting under a pressure of 0.5 bar of nitrogen with a mixture of cyclohexane and ethyl acetate (70/30 by volume) and collecting 40 cm³ fractions. Fractions 24 to 48 are combined and then concentrated to dryness under reduced pressure (2.7 kPa). 1.21 g of (3aRS,4RS,7aSR)-4-(2-methoxyphenyl)-2-(3-indolylacetyl)-4-perhydroisoindolol are obtained in the form of an off-white foam.

Proton NMR spectrum (DMSO $d_6$):

2.9 (vb, 1H, $H_{3a}$); 3.6 (bs, 2H, $CH_2CO$); 3.8 (s, 3H, $OCH_3$); 6.9 to 7.5 (m, 9H aromatic).

IR spectrum (KBr—characteristic bands in $cm^{-1}$):

3540, 3470, 3000–2850, 2835, 1635, 1580, 1490, 1450, 1235, 1060, 1035.

EXAMPLE 7

By working according to the experimental procedure of Example 8 below, from 0.72 g of (3aRS,4RS,5RS,7aSR)-4-(2-methoxyphenyl)-4,5-perhydroisoindolediol and 0.54 g of 2-(S)-(2-methoxyphenyl)propionic acid, and after purification on a column of alumina (particle size 50–150 μm, height=30 cm, diameter=4 cm), eluting with ethyl acetate and then with a mixture of dichloromethane and methanol (99/1 by volume),0.17 g of (3aR*,4R*,5R*,7aS*)-4-(2methoxyphenyl)-2-[2-(S)-(2-methoxyphenyl)]-4,5-perhydroisoindolediol is obtained, melting at 107–109° C.

(3aRS,4RS,5RS,7aSR)-4-(2-Methoxyphenyl)-4,5-perhydroisoindolediol may be prepared in the following way:

A mixture of 1.5 g of (3aRS,4RS,5RS,7aSR)-2-benzyl-4-(2-methoxyphenyl)-4,5-perhydroisoindolediol and 120 cm³ of anhydrous ethanol is heated to 60° C. with stirring; 0.49 g of 20% palladium hydroxide on charcoal is added and the reaction mixture is then hydrogenated, with stirring, at a temperature of 60° C. and at atmospheric pressure. After reaction for 2 hours, the theoretical volume of hydrogen has been absorbed; the reaction mixture is filtered and then concentrated to dryness under reduced pressure (2.7 kPa). The residue is crystallized in 50 cm³ of isopropyl ether. 1.02 g of (3aRS,4RS,5RS,7aSR)-4-(2-methoxyphenyl)-4,5-perhydroisoindolediol are obtained, melting at 168° C.

(3aRS,4RS,5RS,7aSR)-2-Benzyl-4-(2-methoxyphenyl)-4,5-perhydroisoindolediol may be prepared in the following way:

To a suspension of 27.6 g of 2-methoxyphenylmagnesium bromide in 60 cm³ of tetrahydrofuran are added dropwise, at room temperature and with stirring, a solution of 4.7 g of (3aRS,5RS,7aSR)-5-acetoxy-2-benzyl-4-perhydroisoindolone in 90 cm³ of tetrahydrofuran. The reaction mixture is stirred at room temperature for 3 hours, treated with 200 cm³ of saturated aqueous ammonium chloride solution and taken up in 200 cm³ of ethyl ether and 100 g of ice. The organic phase is separated out after settling has taken place, dried over magnesium sulphate, filtered and concentrated to dryness under reduced pressure (2.7 kPa). The residue is crystallized in 80 cm³ of petroleum ether and then chromatographed on a column of silica gel (particle size 0.04–0.06 mm, diameter 1 cm, height 20 cm), eluting under a pressure of 0.5 bar of nitrogen with a mixture of dichloromethane and methanol (95/5 by volume) and collecting 25 cm³ fractions. Fractions 14 to 21 are combined and then concentrated to dryness under reduced pressure (2.5 kPa). 1.55 g of (3aRS,4RS,5RS,7aSR)-2-benzyl-4-(2-methoxyphenyl)-4,5-perhydroisoindolediol are obtained, melting at 140° C.

(3aRS,5RS,7aSR)-5-Acetoxy-2-benzyl-4-perhydroisoindolone may be prepared in the following way:

To a solution of 7.5 g of 6-acetoxy-2-cyclohexenone and 16.83 cm³ of N-butoxymethyl-N-trimethylsilylmethylbenzylamine in 150 cm³ of dichloromethane are added, at a temperature of 10° C., 12 drops of trifluoroacetic acid. The reaction mixture is stirred at room temperature for 7 hours, then 2 g of potassium carbonate are added and the solution is filtered through a sinter funnel and concentrated to dryness under reduced pressure (2.7 kPa). The residue is chromatographed on a column of silica gel (particle size 0.04–0.06 mm, diameter 6 cm, height 35 cm), eluting under a pressure of 0.5 bar of nitrogen with a mixture of dichloromethane and methanol (97.5–2.5 by volume) and collecting 60 cm³ fractions. Fractions 25 to 39 are combined and concentrated to dryness under reduced pressure (2.7 kPa). 6.25 g of (3aRS,5RS,7aSR)-5-acetoxy-2-benzyl-4-perhydroisoindolone are obtained in the form of a yellow oil.

N-Butoxymethyl-N-trimethylsilylmethylbenzylamine may be prepared according to the method of Y. Tarao et al., Chem. Pharm. Bull., 33, 2762, (1985).

6-Acetoxycyclohexenone may be prepared according to the method described by G. M. Rubottom et al., J. Org. Chem., 1978, 43, 1599.

EXAMPLE 8

To a solution of 0.25 g of (3aRS,4RS,5RS,7aSR)-4-(2-methoxyphenyl)-4,5-perhydroisoindolediol and 0.18 g of 3-indoleacetic acid in 35 cm³ of dichloromethane, cooled to 0° C., are added 5 mg of 1-hydroxybenzotriazole, 0.22 g of 1-(3-dimethylaminopropyl)-3-ethylcarbodiimide hydrochoride and 0.33 cm³ of diisopropylethylamine. The mixture is stirred for 15 hours at room temperature, 40 cm³ of dichloromethane are added and the organic phase is washed with 3 times 60 cm$^3$ of water, dried over magnesium sulphate and concentrated to dryness under reduced pressure (2.7 kPa). The cream-coloured foam obtained is chromatographed on a column of silica gel (particle size 0.04–0.06 mm, diameter 1 cm, height 30 cm), eluting under a pressure of 0.5 bar of nitrogen with a mixture of dichloromethane and methanol (93/7 by volume) and collecting 25 cm$^3$ fractions. Fractions 7 to 10 are combined and are then concentrated to dryness under reduced pressure (2.7 kPa). 0.35 g of (3aRS, 4RS,5RS,7aSR)-4-(2-methoxyphenyl)-2-[(3-indolyl)acetyl] -4,5-perhydroisoindoledio is obtained, melting at 166° C.

EXAMPLE 9

To a suspension of 2.61 g of 2-methoxyphenylmagnesium bromide in 10 cm$^3$ of tetrahydrofuran, cooled to 15° C., is added, dropwise and with stirring, a solution of 1.3 g of (3aRS,7aRS)-7,7-dimethyl-2-[(2-methoxyphenyl)acetyl]-4-perhydroisoindolone in 30 cm$^3$ of tetrahydrofuran, followed by 2 g of anhydrous cerium chloride. The reaction mixture is stirred at room temperature for 18 hours, treated with 80 cm$^3$ of saturated aqueous ammonium chloride solution, taken up in 100 cm$^3$ of ethyl acetate and washed with 100 cm$^3$ of saturated aqueous sodium chloride solution. The organic phase is separated out after settling has taken place, dried over magnesium sulphate, filtered and concentrated to dryness under reduced pressure (2.7 kPa). The residue is chromatographed on a column of silica gel (particle size 0.04–0.06 mm, diameter 3.6 cm, height 22 cm), eluting under a pressure of 0.5 bar of nitrogen with a mixture of cyclohexane and ethyl acetate (70/30 by volume) and collecting 50 cm$^3$ fractions. Fractions 47 to 54 are combined and then concentrated to dryness under reduced pressure (2.5 kPa). The residue is crystallized in 1 cm$^3$ of acetonitrile. 0.177 g of (3aRS,4RS,7aRS)-7,7-dimethyl-4-(2-methoxyphenyl)-2-[(2-methoxyphenyl)acetyl]-4-perhydroisoindolol is obtained, in the form of white crystals melting at 187° C.

(3aRS,7aRS)-7,7-Dimethyl-2-[(2methoxyphenyl)acetyl]-4-perhydroisoindolone may be prepared in the following way:

By working according to the experimental procedure of Example 6, from 2.17 g of (3aRS,7aRS)-7,7-dimethyl-4-perhydroisoindolone hydrochloride and 2.12 g of 2-methoxyphenylacetic acid and by adding 1.37 g of diisopropylethylamine, and after purification on a column of silica gel (particle size 0..04–0.06 mm, diameter 3.6 cm, height 20 cm), 0.9 g of (3aRS,7aRS)-7-dimethyl-2-[(2-methoxyphenyl) acetyl]-4perhydroisoindolone is obtained, in the form of white crystals melting at 128° C.

(3aRS,7aRS)-7,7-Dimethyl-4-perhydroisoindolone hydrochloride may be prepared in the following way:

A mixture of 2.31 g of (3aRS,7aRS)-2-benzyl-7,7-dimethyl-4-perhydroisoindolone and 9.96 cm$^3$ of 1N hydrochloric acid in 25 cm$^3$ of anhydrous ethanol is heated to 60° C. with stirring; 0.11 g of 20% palladium hydroxide on charcoal is added and the reaction mixture is then hydrogenated, with stirring, at a temperature of 60° C. and at atmospheric pressure. After reaction for 6 hours, the reaction mixture is filtered and then concentrated to dryness under reduced pressure (2.7 kPa). 2.17 g of (3aRS,7aRS)-7,7-dimethyl-4-perhydroisoindolone hydrochloride are obtained, in the form of a pink oil containing ethanol.

(3aRS,7aRS)-2-Benzyl-7,7-dimethyl-4-perhydroisoindolone may be prepared in the following way:

To a solution of 5 g of 4,4-dimethylcyclohex-2-enone and 12.4 cm$^3$ of N-butoxymethyl-N-trimethylsilylmethylbenzylamine in 100 cm$^3$ of dichloromethane are added, at a temperature of 10° C., 5 drops of trifluoroacetic acid. The reaction mixture is stirred at this temperature for 3 hours, then potassium carbonate is added and the solution is filtered through a sinter funnel and concentrated to dryness under reduced pressure (2.7 kPa). The residue is chromatographed on a column of silica gel (particle size 0.04–0.06 mm, diameter 5.2 cm, height 25 cm), eluting under a pressure of 0.5 bar of nitrogen with a mixture of cyclohexane and ethyl acetate (85/15 by volume) and collecting 100 cm$^3$ fractions. Fractions 39 to 63 are combined and concentrated to dryness under reduced pressure (2.7 kPa). 3.64 g of (3aRS,7aRS)-2-benzyl-7,7-dimethyl-4-perhydroisoindolone are obtained in the form of a yellow oil.

EXAMPLE 10

By working according to the experimental procedure of Example 9, from 0.78 g of 7,7-dimethyl-2-[2-(S)-(2-methoxyphenyl)propionyl]-4-perhydroisoindolone (mixture of (3aR,7aR) and (3aS,7aS) diastereoisomers) and 1.5 g of 2-methoxyphenylmagnesium bromide, and after purification on a column of silica gel (particle size 0.04–0.06 mm, diameter 2.8 cm, height 21 cm), 0.27 g of (3aR*,4R*,7aR*) -7,7-dimethyl-4-(2-methoxyphenyl)-2-[2-(S)-(2-methoxyphenyl)propionyl]-4-perhydroisoindolol is obtained, in the form of a white foam.

Proton NMR spectrum (DMSO d$_6$):

1.1–1.15–1 and 0.9 (4a, 4 CH$_3$); 1.25 and 1.17 (2, J=7, 2 CH$_3$—CH); 3.85—3.8.78 and 3.6 (4s, 4 OCH$_3$); 6.7 to 7.6 (m, 8H, aromatic).

IR spectrum (KBr—characteristic bands in cm$^{-1}$):

3400, 3100–3000, 3000–2850, 2835, 1630, 1600, 1585, 1495, 1245, 1065, 1035, 755.

7,7-Dimethyl-2-[2-(S)-(2-methoxyphenyl)propionyl[-4-perhydroisoindolone (mixture of (3aR,7aR) and (3aS,7aS) diastereoisomers) may be obtained in the following way:

By working according to the experimental procedure of Example 6, from 1 g of (3aRS,7aRS)-7,7-dimethyl-4-(S)-(2-(2-methyoxphenyl propionic acid, and after purification on a column of silica gel (particle size 0.04–0.06 mm, diameter 3.2 cm, height 20.5 cm), 0.96 g of 7,7-dimethyl-2-[2-(S)-(2-methoxyphenyl)propionyl]-4-perhydroisoindolone (mixture of (3aR, 7aR) and (3aS, 7aS) diastereoisomers) is obtained in the form of a colourless oil.

EXAMPLE 11

By working according to the experimental procedure of Example 6, from 0.6 g of (3aRS, 4RS, 7aRS)-7,7-dimethyl-4-(2-methoxyphenyl)-4-perhydroisoindolol and 0.41 g of 2-dimethylaminophenylacetic acid, and after purification on a column of silca gel (particle size 0.04–0.06 m, diameter 2.8 cm, height 17 cm), 0.4 g of (3aRS,4RS,7aRS)-7,7-dimethyl-4-(2-methoxyphenyl)-2-[(2-dimethylaminophenyl)acetyl]-4-perhydroisoindolol is obtained, in the form of a white foam.

Proton NMR spectrum (DMSO d$_6$):

1 (s,3H, CH$_3$); 1.2 (s, 3H, CH$_3$); 2.6 (ms, 6H, N(CH$_3$)$_2$); 3 (dd, J=6.5 and 6, 1H, H$_{7a}$ or H$_{3a}$); 3.1 (ms, 1H); 3.4 (d, J=11, 1H); 3.5 (mt, 4H); 3.85 (s, 3H, OCH$_3$); 6.9 to 7.5 (m, 8H aromatic).

IR spectrum (KBr—characteristic bands in cm$^{-1}$):

3580, 3000–2850, 2835, 2790, 1630, 1595, 1580, 1495, 1455, 1240, 1065, 1035.

(3aRS,4RS,7aRS)-7,7-Dimethyl-4-(2-methoxyhenyl)-4-perhydroisoindolol hydrochloride may be prepared in the following way:

To a solution of 1.49 g of (3aRS,4RS,7aRS)-7,7-dimethyl-4-(2-methoxyphenyl)-2-t-butyloxycarbonyl-4-perhydroisoindolol in 21 cm³ of dioxane are added 35 cm³ of 7.4 N hydrochloric acid solution in dioxane. The reaction mixture is stirred for 1 hour at room temperature and then concentrated to dryness under reduced pressure (2.7 kPa). 1.47 g of (3aRS,4RS,7aRS)-7,7-dimethyl-4-(2-methoxyphenyl)-4-perhydroisoindolol hydrochloride are obtained in the form of a white foam.

(3aRS,4RS,7aRS)-7,7-dimethyl-4-(2-methoxyphenyl)-2-t-butyloxycarbonyl-4-perhydroisoindolol may be prepared in the following way:

By working according to the experimental procedure of Example 9, from 4.4 g of 2-methoxyphenylmagnesium bromide and 1.86 g of (3aRS,7aRS)-7,7-dimethyl-2-t-butyloxycarbonyl-4-perhydroisoindolone, 2.6 g of (3aRS,7aRS)-7,7-dimethyl-4-(2-methoxyphenyl)-2-t-butyloxycarbonyl-4-perhydroisoindolol are obtained, in the form of white crystals melting at 178° C.

(3aRS,7aRS)-7,7-Dimethyl-2-t-butyloxycarbonyl-4-perhydroisoindolone may be prepared in the following way:

To a solution of 3 g of (3aRS,7aRS)-7,7-dimethyl-4-perhydroisoindolone hydrochloride and 1.49 g of triethylamine in 80 cm³ of dry dichloromethane are added 3.56 g of di-tert-butyl dicarbonate, followed by 0.18 g of 4-dimethylaminopyridme. The reaction mixture is stirred at room temperature for 1 hour and then washed twice with 100 cm³ of aqueous citric acid solution, then with 100 cm³ of saturated aqueous sodium hydrogen carbonate solution and then with 100 cm³ of saturated aqueous sodium chloride solution. The organic phase is dried overmagnesium sulphate and then concentrated to dryness under reduced pressure (2.7 kPa). The residue is chromatographed on a column of silica gel (particle size 0.04–0.06 mm, diameter 2.8 cm, height 15 cm), eluting under a pressure of 0.5 bar of nitrogen with a mixture of cyclohexane and ethyl acetate (75/25) and collecting 30 cm³ fractions. Fractions 4 to 9 are combined and concentrated to dryness under reduced pressure (2.7 kPa). 3.07 g of (3aRS,7aRS)-7,7-dimethyl-2-t-butyloxycarbonyl-4-perhydroisoindolone are obtained, in the form of white crystals melting at 130° C.

EXAMPLE 12

By working according to the experimental procedure of Example 6, from 0.6 g of (3aRS,4RS,7aRS)-7,7-dimethyl-4-(2-methoxyphenyl)-4-perhydroisoindolol hydrochloride and 0.4 g of 3-indoleacetic acid, and after purification on a column of silica gel (particle size 0.04–0.06 mm, diameter 2.4 cm, height 15 cm), 0.17 g of (3aRS,4RS,7aRS)-7,7-dimethyl-4-(2-methoxyphenyl)-2-(3-indolylacetyl)-4-perhydroisoindolol is obtained, in the form of a white foam.

Proton NMR spectrum (DMSO-$d_6$):

1 (s, 3H, $CH_3$); 1.2 (s, 3H, $CH_3$); 2.65 (ddd, J=15, 14 and 4.5, 1H, $H_5$); 3 (broad dd, J=6.5 and 6, $H_{7a}$ or $H_3a$); 3.65 (broad s, 2H, $CH_2CO$); 3.9 (s, 3H, $OCH_3$); 6.9 to 7.6 (m, 9H, aromatic).

IR spectrum (KBr—characteristic bands in cm$^{-1}$):
3580, 3475, 3000–2850, 2835, 1630, 1595, 580, 1485, 1450, 1240, 1065, 1035.

EXAMPLE 13

By working according to the experimental procedure of Example 8, from 1.24 g of (3aRS,4RS,5RS,7aRS)-7,7-dimethyl-4-(2-methoxyphenyl)-4,5-perhydroisoindolediol and 0.85 g of 2-(S)-(2-methoxyphenyl)propionic acid, and after purification on a column of silica gel (particle size 0.04–0.06 mm, height 20 cm, diameter 3 cm), 0.46 g of (3aR*,4R*,5R*,7aS*)-7,7-dimethyl-4-(2-methoxyphenyl)-2-]2-(S)-(2-methoxyphenyl) propionyl]-4,5-perhydroisolndolediol is obtained, melting at 194° C.

(3aRS,4RS,5RS,7aRS)-7,7-Dimethyl-4-(2-methoxyphenyl)-4,5-perhydroisoindolediol may be prepared in the following way:

A mixture of 2.7 g of (3aRS,4RS,5RS,7aRS)-2-benzyl-7,7-dimethyl-4-(2-methoxyphenyl)-4,5-perhydroisoindolediol and 75 cm³ of anhydrous ethanol is heated to 60° C. with stirring; 0.8 g of 20% palladium hydroxide on charcoal is added and the reaction mixture is then hydrogenated, with stirring, at a temperature of 60° C. and at atmospheric pressure. After reaction for 1 hour, the theoretical volume of hydrogen has been absorbed; the reaction mixture is filtered and then concentrated to dryness under reduced pressure (2.7 kPa). The residue is crystallized in 15 cm³ of isopropyl ether. 1.74 g of (3aRS,4RS,5RS,7aRS)-7,7-dimethyl-4-(2-methoxyhenyl)-4,5-perhydroisoindolediol are obtained, melting at 208° C.

(3aRS,4RS,5RS,7aRS)-2-Benzyl-7,7-dimethyl-4-(2-methoxyphenyl)-4,5-perhydroisoindolediol may be prepared in the following way:

To a suspension of 33.8 g of 2-methoxyphenylmagnesium bromide in 75 cm³ of tetrahydrofuran is added dropwise, at room temperature and with stirring, a solution of 6.6 g of (3aRS,5RS,7aRS)-5-acetoxy-2-benzyl-7,7-dimethyl-4-perhydroisoindolone in 75 cm³ of tetrahydrofuran. The reaction mixture is stirred at room temperature for 15 hours, treated with 200 cm³ of saturated aqueous ammonium chloride solution and taken up in 200 cm³ of ethyl ether and 100 g of ice. The organic phase is extracted with 3 times 100 cm³ of ethyl ether, dried over magnesium sulphate, filtered and concentrated to dryness under reduced pressure (2.7 kPa). The residue is crystallized in 500 cm³ of petroleum ether. 2.8 g of (3aRS,4RS,5RS,7aRS)-2-benzyl-7,7-dimethyl-4-(2-methoxyphenyl)-4,5-perhydroisoindolediol are obtained, melting at 190° C.

(3aRS,5RS,7aRS)-5-Acetoxy-2-benzyl-7,7-dimethyl-4-perhydroisoindolone may be prepared in the following way:

To a solution of 23.2 g of 6-acetoxy-4,4-dimethylcyclohex-2-enone and 0.8 cm³ of trifluoroacetic acid in 770 cm³ of dichloromethane are added, at room temperature, 43 cm³ of N-butoxymethyl-N-trimethylsilylmethylbenzylamine. The reaction mixture is stirred at room temperature for 15 hours then 5 g of potassium carbonate are added and the solution is filtered through a sinter funnel and concentrated to dryness under reduced pressure (2.7 kPa). The residue is chromatographed on a column of silica gel (particle size 0.04–0.06 mm, diameter 8 cm, height 53 cm), eluting under a pressure of 0.5 bar of nitrogen with a mixture of ethyl acetate and cyclohexane (20/80 by volume) and collecting 250 cm³ fractions. Fractions 18 to 27 are combined and concentrated to dryness under reduced pressure (2.7 kPa). 6.6 g of (3aRS,5RS,7aRS)-5-acetoxy-2-benzyl-7,7-dimethyl-4-perhydroisoindolone are obtained in the form of a yellow oil.

N-Butoxymethyl-N-trimethylsilylmethylbenzylamine may be prepared according to the method of Y. Tarao et al., Chem. Pharm. Bull., 33, 2762, (1985).

6-Acetoxy-4,4-dimethylcyclohexenone may be prepared according to the method described by D. S. Watt et al., Tetrahedron Lett., 1984, 25, 5839.

EXAMPLE 14

To a solution of 0.44 g of (3aRS,4RS,5RS,7aRS)-7,7-dimethyl-4-(2-methoxyphenyl)-4,5-perhydroisoindolediol and 0.29 g of 3-indoleacetic acid in 40 cm$^3$ of dichloromethane, cooled to 0° C., are added 5 mg of 1-hydroxybenzotriazole, 0.35 g of 1-(3-dimethylaminopropyl)-3-ethylcarbodiimide hydrochloride and 0.42 cm$^3$ of diisopropylethylamine. The mixture is stirred for 15 hours at room temperature, 100 cm$^3$ of dichloromethane are added and the organic phase is washed with 50 cm$^3$ of aqueous sodium bicarbonate solution and with 60 cm$^3$ of saturated aqueous sodium chloride solution, dried over magnesium sulphate and concentrated to dryness under reduced pressure (2.7 kPa). The cream-coloured foam obtained is chromatographed on a column of silica gel (particle size 0.04–0.06 mm, diameter 1 cm, height 30 cm), eluting under a pressure of 0.5 bar nitrogen with a mixture of dichloromethane and methanol (97/3 by volume) and collecting 30 cm$^3$ fractions. Fractions 5 to 7 are combined and then concentrated to dryness under reduced pressure (2.7 kPa); the solid obtained is recrystallized in 5 cm$^3$ of isopropyl ether. 0.48 g of (3aRS,4RS,5RS,7aRS)-7,7-dimethyl-4-(2-methoxyphenyl)-2-[(3-indolyl)acetyl]-4,5-perhydroisoindolediol is obtained, melting at 160–165° C.

EXAMPLE 15

To a suspension of 2-methoxyphenylmagnesium bromide, prepared from 0.576 g of magnesium and 4.5 g of 2-bromoanisole in 25 cm$^3$ of tetrahydrofuran, is added dropwise, with stirring and at 30° C., a solution of 1.6 g of (3aRS,7SR,7aRS)-7-methyl-7-phenyl-2-[(2methoxyphenyl)acetyl]-4-perhydroisoindolone in 40 cm$^3$ of tetrahydrofuran. The reaction mixture is stirred at room temperature for 18 hours, treated with 100 cm$^3$ of saturated aqueous ammonium chloride solution, taken up in 100 cm$^3$ of ethyl acetate and washed with 100 cm$^3$ of water and then with 100 cm$^3$ of saturated aqueous sodium chloride solution. The organic phase is separated out after settling has taken place, dried over magnesium sulphate, filtered and concentrated to dryness under reduced pressure (2.7 kPa). The residue is chromatographed on a column of silica gel (particle size 0.04–0.06 mm, diameter 3 cm, height 16 cm), eluting under a pressure of 0.5 bar of nitrogen with a mixture of cyclohexane and ethyl acetate (70/30 by volume) and collecting 35 cm$^3$ fractions. Fractions 8 to 16 are combined and then concentrated to dryness under reduced pressure (2.5 kPa). The residue is crystallized in 4 cm$^3$ of ethyl acetate. 0.6 g of (3aRS,4RS,7SR,7aRS)-7-methyl-7-phenyl-4-(2-methoxyphenyl)-2-[(2-methoxyphenyl)acetyl]-4perhydroisoindolol is obtained, in the form of white crystals melting at 234° C.

(3aRS,7SR,7aRS)-7-Methyl-7-phenyl-2-[(2methoxyphenyl)acetyl]-4-perhydroisoindolone may be prepared in the following way:

To a solution of 1.66 g of 2-methoxyphenylacetic acid in 40 cm$^3$ of dichloromethane are added, at 4° C., 1.62 g of N,N'-carbonyldiimidazole. Stirring for 30 minutes at room temperature is followed by dropwise addition of a solution containing 1.85 g of (3aRS,7SR,7aRS)-7-methyl-7-phenyl-4-perhydroisoindolone hydrochloride and 0.7 g of triethylamine in 30 cm$^3$ of dichloromethane. After stirring for 2 hours, the reaction mixture is washed twice with 50 cm$^3$ of water and then with 50 cm$^3$ of saturated aqueous sodium chloride solution. The organic phase is separated out after settling has taken place, dried over magnesium sulphate, filtered and concentrated to dryness under reduced pressure (2.7 kPa). The residue is chromatographed on a column of silica gel (particle size 0.04–0.06 mm, diameter 3 cm, height 15 cm), eluting under a pressure of 0.5 bar of nitrogen with a mixture of cyclohexane and ethyl acetate (80/20 by volume) and collecting 50 cm$^3$ fractions. Fractions 16 to 60 are combined and then concentrated to dryness under reduced pressure (2.5 kPa). The residue is crystallized in 30 cm$^3$ of ethyl acetate. 1.3 g of (3aRS,7SR,7aRS)-7-methyl-7-phenyl-2-[(2-methoxyphenyl)acetyl]-4-perhydroisoindolone are obtained, in the form of white crystals melting at 160° C.

(3aRS,7SR,7aRS)-7-Methyl-7-phenyl-4-perhydroisoindolone hydrochloride may be prepared in the following way:

4.27 g of (3aRS,7SR,7aRS)-7-methyl-7-phenyl-2-vinyloxycarbonyl-4-perhydroisoindolone are dissolved in 100 cm$^3$ of hydrochloric acid-saturated tetrahydrofuran. After stirring for one hour at room temperature, the solution is concentrated to dryness under reduced pressure (2.7 kPa). The residue is taken up in 100 cm$^3$ of absolute ethanol and heated for one hour at 60° C. After evaporation of the solvent under reduced pressure (2.7 kPa), 3.71 g of (3aRS,7SR,7aRS)-7-methyl-7-phenyl-4-perhydroisoindolone hydrochloride are obtained in the form of a yellow oil.

(3aRS,7SR,7aRS)-7-Methyl-7-phenyl-2-vinyloxycarbonyl-4-perhydroisoindolone may be prepared in the following way:

To a solution of 9 g of (3aRS,7SR,7aRS)-2-benzyl-7-methyl-7-phenyl-4-perhydroisoindolone in 100 cm$^3$ of 1,2-dichloroethane are added, at room temperature, 2.84 cm$^3$ of vinyl chloroformate, followed by heating for 2 hours at reflux. The solution is concentrated to dryness under reduced pressure (2.7 kPa) and the residue is purified by chromatography on a Column of silica gel (particle size 0.04–0.06 mm, diameter 4 cm, height 23 cm), eluting under a pressure of 0.5 bar of nitrogen with a mixture of cyclohexane and ethyl acetate (90/10 by volume) and collecting 100 cm$^3$ fractions. Fractions 17 to 34 are combined and concentrated to dryness under reduced pressure (2.7 kPa). 4.27 g of (3aRS,7SR,7aRS)-7-methyl-7-phenyl-2-vinyloxycarbonyl-4-perhydroisoindolone are obtained in the form of a yellow oil.

(3aRS,7SR,7aRS)-2-Benzyl-7-methyl-7-phenyl-4-perhydroisoindolone may be prepared in the following way:

To a solution of 14.5 g of 4-methyl-4-phenylcyclohex-2-enone and 24.45 cm$^3$ of N-butoxymethyl-N-trimethylsilylmethylbenzylamine in 65 cm$^3$ of dichloromethane are added, at a temperature of 25° C., 3 drops of trifluoroacetic acid. The reaction mixture is stirred at this temperature for 30 minutes and then heated to reflux for 2 hours. After cooling, 10 g of potassium carbonate are added, the mixture is stirred for 15 minutes and the solution is then filtered through a sinter funnel and concentrated to dryness under reduced pressure (2.7 kPa). The residue is chromatographed on a column of silica gel (particle size 0.04–0.06 mm, diameter 5 cm, height 39 cm), eluting under a pressure of 0.5 bar of nitrogen with a mixture of cyclohexane and ethyl acetate (80/20 by volume) and collecting 100 cm$^3$ fractions. Fractions 8 to 30 are combined and concentrated to dryness under reduced pressure (2.7 kPa). 9 g of (3aRS,7SR,7aRS)-2-benzyl-7-methyl-7-phenyl-4-perhydroisoindolone are obtained in the form of a yellow oil.

N-Butoxymethyl-N-trimethylsilylmethylbenzylamine may be prepared according to the method of Y. Terao et al., Chem. Pharm. Bull., 33, 2762, (1985).

4-Methyl-4-phenylcyclohex-2-enone may be prepared according to the method of H. E. Zimmerman and G. Jones, J. Amer. Chem. Soc., 92(9), 2753, (1970).

EXAMPLE 16

To a solution of 0.52 g of 2-methoxyphenylacetic acetic acid in 20 cm³ of dichloromethane, cooled to 0° C., are added 0.5 g of N,N'-carbonyldiimidazole followed, after stirring for 45 minutes at 0° C., by addition of 0.74 g of (3aRS,4RS,5RS,7aSR)-4-(2-methoxyphenyl)-5-methyl-4-perhydroisoindolol. The mixture is stirred for 18 hours at room temperature and the organic phase is then washed with twice 40 cm³ of water, then with 40 cm³ of saturated aqueous sodium chloride solution, dried over magnesium sulphate and concentrated to dryness under reduced pressure (2.7 kPa). The residue is chromatographed on a column of silica gel (particle size 0.04–0.06 mm, diameter 2 cm, height 15 cm), eluting under a pressure of 0.5 bar of nitrogen with a mixture of cyclohexane and ethyl acetate (80/20 by volume) and collecting 25 cm³ fractions. Fractions 10 to 20.are combined and then concentrated to dryness under reduced pressure (2.7 kPa). The residue is crystallized in acetonitrile. 0.5 g of (3aRS,4RS, 5RS, 7aSR)-4-(2-methoxyphenyl)-2-(2-methoxyphenylacetyl)-5-methyl-4-perhydroisoindolol is obtained, in the form of white crystals melting at 198° C.

(3aRS,4RS, 5RS, 7 aSR)-4-(2-methoxyphenyl)-5-methyl-4-perhydroisoindolol may be prepared in the following way:

To a solution of I g of (3aRS,4RS,5RS,7aSR)-2-benzyl-4-(2-methoxyphenyl)-5-methyl-4-perhydroisoindolol in 15 cm³ of anhydrous ethanol are added 2 g of 20% palladium hydroxide on charcoal and the reaction mixture is then hydrogenated, with stirring, at a temperature of 60° C. and at atmospheric pressure. After reaction for 1 hour, the reaction mixture is filtered and then concentrated to dryness under reduced pressure (2.7 kPa). 0.74 g of (3aRS,4RS, 5RS, 7aSR)-4-(2-methoxyphenyl)-5-methyl-4-perhydroisoindolol is obtained in the form of a yellow foam.

IR spectrum (KBr—characteristic bands in cm⁻¹): 3425, 3075–3025–3000, 2955, 2880, 2835, 1595–1500–1485, 1460, 1375, 1235, 1025, 750.

(3aRS,4RS,5RS,7aSR)-2-Benzyl-4-(2-methoxyphenyl)-5-methyl-4-perhydroisoindolol may be prepared in the following way:

To a suspension of 2.13 g of 2-methoxyphenylmagnesium bromide in 15 cm³ of tetrahydrofuran is added dropwise, at room temperature and with stirring, a solution of 0.7 g of (3aRS,5RS,7aSR)-2-benzyl-5-methyl-4-perhydroisoindolone in 15 cm³ of tetrahydrofuran. The reaction mixture is stirred at room temperature for 48 hours, treated with 50 cm³ of saturated aqueous ammonium chloride solution, taken up in ethyl acetate and washed with saturated aqueous sodium chloride solution. The organic phase is separated out after settling has taken place, dried over magnesium sulphate, filtered and concentrated to dryness under reduced pressure (2.7 kPa). The residue is chromatographed on a column of Merck silica gel (particle size 0.04–0.06 mm, diameter 2 cm, height 15 cm), eluting under a pressure of 0.5 bar of nitrogen with a mixture of cyclohexane and ethyl acetate (60/40 by volume) and collecting 25 cm³ fractions. Fractions 10 to 20 are combined and then concentrated to dryness under reduced pressure (2.5 kPa). 1 g of (3aRS,4RS,5RS,7aSR)-2-benzyl-4-(2-methoxyphenyl)-5methyl-4-perhydroisoindolol is obtained in the form of a yellow oil.

(3aRS,5RS,7aSR)-2-Benzyl-5-methyl-4-2-perhydroisoindolone may be prepared in the following way:

To a solution of 1 g of 6-methyl-cyclohex-2-enone in 15 cm³ of dichloromethane are added, at room temperature, 3 drops of trifluoroacetic acid, followed by 3.6 cm³ of N-butoxymethyl-N-trimethylsilylmethylbenzylamine. The reaction mixture is brought to reflux, with stirring, for 3 hours. After cooling, potassium carbonate is added and the solution is filtered through a sinter funnel and concentrated to dryness under reduced pressure (2.7 kPa). The residue is chromatographed on a column of silica gel (particle size 0.04–0.06 mm, diameter 2 cm, height 20 cm), eluting under a pressure of 0.5 bar of nitrogen with a mixture of cyclohexane and ethyl acetate (60/40 by volume) and collecting 25 cm³ fractions. Fractions 10 to 20 are combined and concentrated to dryness under reduced pressure (2.7 kPa). 0.7 g of (3aRS,5RS,7aSR)-2benzyl-5-methyl-4-perhydroisoindolone is obtained in the form of a colourless oil.

6-Methylcyclohex-2-enone may be prepared according to the method of J. Tsuji et al., Tetrahedron Lett., 24, 1797 (1993).

EXAMPLE 17

By working according to the experimental procedure of Example 16, from 4.5 g of 2-(S)-(2-methoxyphenyl) propionic acid and 5 g of (3aRS,4RS,5RS,7aSR)-4-(2-methoxyphenyl)-5-methyl-4-perhydroisoindolol, and after purification on a column of silica gel (particle size 0.04–0.06 mm, diameter 5.4 cm, height 35 cm, eluting under a pressure of 0.5 bar of nitrogen with a mixture of cyclohexane and ethyl acetate (80/20 by volume) and collecting 75 cm³ fractions), 0.84 g (fractions 32 to 40) of (3aR*,4R*,5R*,7aS*)-4-(2-methoxyphenyl)-2-[2-(S)-(2-methoxyphenyl)propionyl]-5-methyl-4-perhydroisoindolol (A form) in the form of a white foam and 0.27 g (fractions 69 to 85) of (3aS*,4S*,5S*,7aR*)-4-(2-methoxphenyl)-2-[2-(S)-(2-methoxyphenyl)propionyl]-5-methyl-4-perhydroisoindolol (B form) in the form of a white foam.

Proton NMR spectrum of the A form (DMSO-d₆+CH₃COOD, T=393° K.): 0.57 (d, 3H, CH₃); 1.3 (d, 3H, CH₃); 1.9–1.3 (m, 4H, 2 CH₂); 2.43 (m, 1H, CH); 2.52 (m, 1H, CH); 2.83 (m, 1H, CH); 3.6–3.1 (m, 4H, 2 CH₂); 3.75 (s, 3H, OCH₃); 3.82 (s, 3H, OCH₃); 4.14 (q, 1H, CH); 7.3–6.8 (m, 8H, aromatic).

IR spectrum of the A form (KBr—characteristic bands in cm⁻¹): 3576, 3436, 3105–3068, 2959–2929–2875, 2836, 1636, 1598–1580–1491, 1457–1435, 1371, 1239, 1062, 1028, 755.

Proton NMR spectrum of the B form (DMSO-d₆+CH₃COOD, T=393° K.): 0.6 (d, 3H, CH₃); 1.31 (d, 3H, CH₃); 1.85–1.3 (m, 4H, 2 CH₂); 2.48 (m, 1H, CH); 2.5 (m, 1H, CH); 2.8 (t, 1H, CH); 3.55–2.9 (m, 4H, 2 CH₂); 3.75 (s, 3H, OCH₃); 3.85 (s, 3H, OCH₃); 4.18 (q, 1H, CH); 7.6–6.85 (m, 8H, aromatic).

IR spectrum of the B form (KBr—characteristic bands in cm⁻¹): 3425, 3106–3068, 2958–2930–2876, 2836, 1626, 1599–1580–1492, 1461–1436, 1378–1370, 1239, 1062, 1028, 755.

EXAMPLE 18

To a solution of 3 g of (3aRS,4RS,6SR,7aSR)-6-hydroxymethyl-4-(2-methoxylphenyl)-4-perhydroisoindolo and 1.8 g of (2-methoxyphenyl)acetic acid in 60 cm³ of dichloromethane are added 2.3 g of 1-(3-dimethylaminopropyl)-3-ethylcarbodiimide hydrochloride. After stirring for 20 hours at 20° C., the reaction mixture is washed with 30 cm³ of water, dried over magnesium sulphate and concentrated to dryness under reduced pressure (2.7 kPa). The residue is chromatographed on a column of silica gel (particle size 0.06–0.20 mm, height 40 cm) in ethyl acetate and then in a mixture of ethyl acetate and methanol (95/5 by volume). After drying under reduced pressure, a white solid is obtained which, after recrystallization in a mixture of ethyl ether and acetonitrile, gives 2.1 g of (3aRS,4RS,6SR,7aSR)-6-hydroxymethyl-4-[(2-methoxy) phenyl]-2-[(2-methoxyphenyl)acetyl]-4-perhydroisoindolol, in the form of white crystals. M.p.=162° C.

Proton NMR spectrum (DMSO $d_6$ +$CH_3COOD$, 250 MHz, T=403° K., δ in ppm): 1.42 and 1.85 (m and d, 2×1H, CH—C$\underline{H}_2$—CH); 1.69 and 2.04 (d and t, 2×1H, C—C$\underline{H}_2$—CH); 2.17 (m, 1H, C$\underline{H}$CH$_2$OH); 2.57 (m, 1H, CH$_2$—C$\underline{H}$CH); 2.85 (t, 1H, CH—C$\underline{H}$—C); 3.17 and 3.40 (m and d, 2×1H, —N—C$\underline{H}_2$—CH); 3.35 (d, 2H, O—C$\underline{H}_2$—CH); 3.47 (s, 2H, CO—C$\underline{H}_2$—Ph); 3.49 (m, 2H, N—C$\underline{H}_2$—CH); 3.75 (s, 3H, OC$\underline{H}_3$); 3.82 (s, 3H, OC$\underline{H}_3$), 6.80–755 (8H, aromatic).

Infra-red spectrum (KBr), characteristic bands (cm$^{-1}$): 3430, 3075, 3000–2875, 2835, 1620, 1605, 1495, 1485, 1460, 1435, 1245, 1055, 1030, 750.

(3aRS,4RS,6SR,7aSR)-6-Hydroxymethyl-4-(2-methoxyphenyl)-4-perhydroisoindolol may be obtained in the following way:

A suspension of 3.1 g of (3aRS,4RS,6SR,7aSR)-2-benzyl-6-hydroxymethyl-4-(2-methoxyphenyl)-4-perhydroisoindolol and 0.5 g of 20% palladium hydroxide on charcoal in 75 cm$^3$ of ethanol is hydrogenated at atmospheric pressure for 3 hours at 60° C. The reaction mixture is subsequently filtered and evaporated to dryness under reduced pressure (2.7 kPa). 3.0 g of (3aRS,4RS, 6SR, 7aSR)-6-hydroxyethyl-4-(2-methoxyphenyl)-4-perhydroisoindolol are obtained in the form of a white foam.

Proton NMR spectrum (DMSO $d_6$ +$CH_3COOD$, 250 MHz, δ in ppm): 1.41 and 1.90 (m and d, 2×1H, CH—C$\underline{H}_2$—CH); 1.60 and 2.22 (d and t, 2×1H, C—C$\underline{H}_2$—CH); 2.10 (m, 1H, C$\underline{H}$—CH$_2$OH); 2.59 (m, 1H, CH$_2$—C$\underline{H}$—CH); 2.95 (m, 1H, CH—C$\underline{H}$—C); 2.95 (m, 2H, N—C$\underline{H}_2$—CH); 3.20 and 3.32 (m, 2H, N—C$\underline{H}_2$—CH), 3.30 (s, 2H, O—C$\underline{H}_2$—CH); 3.81 (s, 3H, OC$\underline{H}_3$); 7.00 to 7.64 (m, 4H, aromatic).

Infra-red spectrum (KBr), characteristic bands (cm$^{-1}$): 3420, 3075, 2920, 2880, 1595, 1575, 1485, 1460, 1235, 1055, 1030, 755.

(3aRS,4RS,6SR,7aSR)-2-Benzyl-6-hydroxymethyl-4-(2-methoxyhenyl)-4-perhydroisoindolol may be prepared in the following way:

To a suspension of 2-methoxyphenylmagnesium bromide (prepared from 24.9 cm$^3$ of 2-bromoanisole and 4.86 g of magnesium) in 200 cm$^3$ of anhydrous tetrahydrofuran is added a solution of 8.0 g of (3aRS,6SR,7aSR)-6-acetoxymethyl-2-benzyl-4-perhydroisoindolone in 60 cm$^3$ of anhydrous tetrahydrofuran. The reaction mixture is stirred for 20 hours at 20° C. and then cooled to +5° C. and treated with 120 cm$^3$ of saturated aqueous ammonium chloride solution and 100 cm$^3$ of ethyl acetate. After filtration of the mixture, the organic phase is washed with brine and then dried over magnesium sulphate and concentrated to dryness under reduced pressure (2.7 kPa). The residue is chromatographed on a column of silica gel (particle size 0.06–0.200 mm, height 40 cm) in a mixture of 1,2-dichloroethane and methanol (95/5 by volume). After recrystallization in ethyl ether, 3.2 g of (3aRS,4RS,6SR, 7aSR)-2-benzyl-6-hydroxymethyl-4-(2-methoxyphenyl)-4-perhydroisoindolol are obtained, in the form of a white solid melting at 110° C.

Proton NMR spectrum (CDCl$_3$+CH$_3$COOD, 250 MHz, T=333° K., δ in ppm): 1.40 and 1.85 (m and d, 2×1H, CH—C$\underline{H}_2$—CH); 1.75 and 2.05 (t and d, 2×1H, C—C$\underline{H}_2$—CH); 2.28 (m, 1H, CH$_2$—C$\underline{H}$—CH$_2$); 2.82 (m, 1H, CH$_2$—C$\underline{H}$—CH); 3.03 (t, 1H, CH—C$\underline{H}$—C); 3.11 and 3.50 (d, 2×1H, N—C$\underline{H}_2$—CH); 3.38 and 3.52 (t, 2×1H, N—C$\underline{H}_2$—CH); 3.50 (m, 2H, O—C$\underline{H}_2$—CH); 3.86 (s, 3H, OC$\underline{H}_3$); 4.28 and 4.40 (d, 2×1H, N—C$\underline{H}_2$Ph); 6.85–7.45 (m, 9H, aromatic).

Infra-red spectrum (KBr), characteristic bands (cm$^{-1}$): 3560, 3420, 3060, 3025, 3005, 2910, 2850, 2800, 1590, 1575, 1495, 1480, 1230, 1055, 1030, 755, 735, 700.

(3aRS,6SR,7aSR)-6-Acetoxymethyl-2-benzyl-4-perhydroisoindolone may be prepared in the following way:

To a solution of 6.5 g of 5-acetoxymethyl-2-cyclohexen-1-one [J. Am. Chem. Soc., 110, 2919 (1988)]and 14 g of N-butoxymethyl-N-trimethylsilylmethylbenzylamine in 60 cm$^3$ of dry dichloromethane are added 2 drops of trifluoroacetic acid. The reaction mixture reaches reflux and is maintained at the same temperature for 30 minutes and is then left at 20° C. for one hour. After addition of 1.0 g of potassium carbonate, the suspension obtained is filtered and the filtrate is concentrated to dryness under reduced pressure (2.7 kPa). The oily residue obtained is chromatographed on a column of silica gel (particle size 0.06–0.2 mm, height 42 cm) in a mixture of cyclohexane and ethyl acetate (40/60 by volume) and then in ethyl acetate. 8.2 g of (3aRS,6SR,7aSR)-6-acetoxymethyl-2-benzyl-4-perhydroisoindolone are obtained in the form of a yellowish oil.

Proton NMR spectrum (CDCl$_3$+CH$_3$COOD, 250 MHz, δ in ppm): 1.82 (m, 2H, CH—C$\underline{H}_2$—CH); 2.03 (s, 3H, C$\underline{H}_3$CO); 2.2 (m, 1H, C$\underline{H}$); 2.27 and 2.42 (t and dd, 2×1H, —COC$\underline{H}_2$—); 2.40 and 3.60 (t, 2×1H, N—C$\underline{H}_2$—CH), 3.10 (td, 1H, C$\underline{H}$); 3.22 (m, 1H, C$\underline{H}$), 3.60 and 3.75 (m, 2×1H, N—C$\underline{H}_2$—CH); 4.00 (m, 2H, O—C$\underline{H}_2$—); 4.10 and 4.23 (d, 2×1H, N—C$\underline{H}_2$-Ph), 7.30–7.45 (m, 5H, aromatic).

Infra-red spectrum (CCl$_4$), characteristic bands (cm$^{-1}$): 3105, 3090, 3065, 3030, 2920, 2795, 1745, 1712, 1605, 1585, 1495, 1455, 1425, 1365, 1240, 1035, 700.

EXAMPLE 19

Proceeding in an identical manner to Example 16, but from 1.46 g of (3aRS,4RS,7SR,7aRS)-7-(hydroxymethyl)-4-(2-methoxyphenyl)-7-methyl-4-perhydroisoindolol and 0.83 g of (2-methoxyphenyl)acetic acid. After chromatography on a column of silica gel (0.060–0.200 mm, diameter 2.5 cm, height 20 cm), eluting under a pressure of 0.5 bar with a mixture of dichloromethane and methanol (91/9 by volume) and collecting 60 cm$^3$ fractions, fractions 2 to 5 are concentrated, recrystallized in acetonitrile and, after drying at 40° C. at 15 Pa, 1.35 g of (3aRS,4RS,7SR,7aRS)-7-(hydroxymethyl)-4-(2methoxyphenyl)-2-[(2-methoxyphenyl)acetyl]-7-methyl-4-perhydroisoindolol are obtained, in the form of a white solid melting at 205° C.

(3aRS,4RS,7SR,7aRS)-7-(Hydroxymethyl)-4-(2-methoxyphenyl)-7-methyl-4-perhydroisoindolol may be prepared in the following way:

A mixture of 3.5 g of (3aRS,4RS,7SR,7aRS)-2-benzyl-7-(hydroxymethyl)-4-(2-methoxyphenyl)-7-methyl-4-perhydroisoindolol, 2.0 g of 20% palladium hydroxide on charcoal and 75 cm$^3$ of ethanol is heated to 50° C. After sparging with hydrogen for two hours, the reaction mixture is cooled to room temperature and flushed with a stream of nitrogen, filtered and concentrated under reduced pressure (2.7 kPa). 1.5 g of (3aRS,4RS,7SR,7aRS)-7-(hydroxymethyl)-4-(2-methoxyphenyl)-7-methyl-4-perhydroisoindolol are obtained in the form Of a white solid.

Proton NMR spectrum (DMSO $d_6$ +$CH_3COOD$, 250 MHz, δ in ppm): 1.05 and 1.80 (2m, 2×1H, C—C $\underline{H}_2$—$CH_2$), 1.20 (s, 3H, $C\underline{H}_3$); 1.45 and 2.75 (d and td, 2×1H, C—$\underline{H}_2$—$CH_2$), 2.20 (m, 1H, $C\underline{H}$—$CH_2$—N); 2.80 and 2.90 (t and dd, 2×1H, $C\underline{H}_2$—N); 3.05 (t, 1H, C—C $\underline{H}$—$CH_2$N); 3.20 (s, 2H, $C\underline{H}_2OH$); 3.20 and 3.40 (t, and d, 2×1H, $C\underline{H}_2$—N), 3.84 (s, 3H, $OC\underline{H}_3$); 3.20 and 3.40 (t and d, 2×1H, $C\underline{H}_2$—N), 3.84 (s, (3aRS,4RS,7SR,7aRS)-2-Benzyl-7-(hydroxymethyl)-4-(2-methoxyphenyl)-7-methyl-4-perhydroisoindolol may be obtained in the following way:

To a suspension of 1.52 g of lithium aluminium hydride in 60 cm³ of tetrahydrofuran are added 8.7 g of 2-benzyl-4,7-ethano-4-(2-methoxyphenyl)-7-methylperhydropyrano [3,4-c]pyrrol-6-one dissolved in 60 cm³ of tetrahydrofuran. After 2 hours at room temperature, 10 cm³ of water are added dropwise, followed by 200 cm³ of ethyl acetate. The mixture obtained is dried over magnesium sulphate, filtered and concentrated to dryness under reduced pressure (2.7 kPa). 7.0 g of (3aRS,4RS,7SR,7aRS)-2-benzyl-7-(hydroxymethyl)-4-(2-methyoxyphenyl)-7-methyl-4-perhydroisoindolol are obtained in the form of a white solid.

Proton NMR spectrum ($CDCl_3$, 250 MHz, δ in ppm): 1.00 and 1.80 (2m, 2×1H, C—$C\underline{H}_2$—$CH_2$), 1.20 (s, 3H, $C\underline{H}_3$), 1.30 and 2.60 (m, 2×1H, C—$CH_2$—$C\underline{H}_2$), 2.25 (m, 1H, C $\underline{H}$—$CH_2N$), 2.30 and 2.65 (m, 2×1H, $C\underline{H}_2$—H), 2.40 and 3.00 (m, 2×1H, $C\underline{H}_2$—N), 3.00 (m, 1H, $C\underline{H}$—$CH_2N$), 3.30 (m, 2H, $C\underline{H}_2OH$), 3.55 and 3.70 (d, 2×1H, N—$C\underline{H}_2Ph$), 3.80 (s, 3H, $OC\underline{H}_3$), 6.80–8.00 (9H aromatic).

2-Benzyl-4,7-ethano-4-(2-methoxyphenyl)-7-methylperhydropyrano [3,4-c]pyrrol-6-one may be prepared in the following way:

To a suspension of 2-methoxyphenylmagnesium bromide in 200 cm³ of tetrahydrofuran, prepared from 18 cm³ of 2-bromoanisole and 3.8 g of magnesium, are added dropwise, at room temperature, 31 g of (3aRS,7SR,7aRS)-7-(allyloxycarbonyl)-2-benzyl-7-methyl-4-perhydroisoindolone dissolved in 100 cm³ of tetrahydrofuran. After one hour at room temperature, 200 cm³ of aqueous 26% ammonium chloride solution are run in over thirty minutes, the reaction mixture is extracted with ethyl acetate and the organic phase is washed with water (2×150 cm³) and then dried over magnesium sulphate, filtered and concentrated under reduced pressure (2.7 kPa). The residue obtained is chromatographed on a column of silica gel (0.060–0.200 mm, diameter 8 cm, height 60 cm), eluting under a pressure of 0.5 bar with a mixture of ethyl acetate and cyclohexane [by volume: 20/80 (4 dm³) then 30/70 (4 dm³) and 40/60 (4 dm³)] and collecting 500 cm³ fractions. Fractions 14 to 22 are combined and concentrated to dryness under reduced pressure (2.7 kPa). 13.1 g of 2-benzyl-4,7-ethano-4-(2-methoxyphenyl)-7-methylperhydropyrano [3,4-c ]pyrrol -6 -one are obtained.

Proton NMR spectrum ($CDCl_3$+$CH_3COOD$, 250 MHz, δ in ppm): 1.15 (s, 3H, $C\underline{H}_3$), 1.80, 1.95 and 2.70 (4H, C $\underline{H}_2$—$C\underline{H}_2$), 2.30 and 3.65 (t and dd, 2×1H, CH—$C\underline{H}_2N$), 2.40 and 3.25 (t, 2H, CH—$C\underline{H}_2$—N), 2.90 (m, 1H, C $\underline{H}$—$CH_2N$), 3.80 (s, 3H, $OC\underline{H}_3$), 3.90 (m, 1H, C $\underline{H}$—$CH_2N$), 3.92 and 4.13 (d, 2×1H, O—$C\underline{H}_2$—CH), 6.80–7.60 (9H aromatic).

(3aRS,7SR,7aRS)-7-Allyloxycarbonyl-2-benzyl-7-methyl-4-perhydroisoindolone may be obtained in the following way:

To a solution of 35 g of 4-allyloxycarbonyl-4-methylcyclohex-2-enone and 65 cm³ of N-butoxymethyl-N-trimethylsilylmethylbenzylamine in 350 cm³ of dichloromethane are added 10 drops of trifluoroacetic acid. The reaction mixture reaches reflux after 15 minutes and then returns slowly (3 hours) to 20° C. 10 g of potassium carbonate are added to the mixture, which is stirred for 30 minutes, filtered and concentrated under reduced pressure (2.7 kPa). The residue obtained is chromatographed on a column of silica gel (0.060–0.200 mm, diameter 9 cm, height 60 cm) eluting under a pressure of 0.5 bar with a mixture of ethyl acetate and cyclohexane [by volume: 30/70 (6 dm³) then 40/60 (6 dm³) and 50/50 (6 dm³)] and collecting 1000 cm³ fractions. From fractions 9 to 15, which are combined and concentrated to dryness under reduced pressure (2.7 kPa), 31 g of (3aRS,7SR,7aRS)-7-allyloxycarbonyl2-benzyl-7-methyl-4-perhydroisoindolone are obtained in oil form.

Proton NMR spectrum ($CDCl_2$ +$CH_3COOD$, 250 MHz, δ in ppm): 1.42 (s, 3H, $C\underline{H}_3$); between 2.00 and 3.80 (10H, 2 times $C\underline{H}$—$CH_2N$, N—$C\underline{H}_2$—CH and C—$CH_2$—$C\underline{H}_2$); 4.50 (d, 2H, O-$C\underline{H}_2$—CH); 5.20 and 5.30 (dd, 2×1H, CH=$C\underline{H}_2$); 5.85 (m, 1H, $C\underline{H}$=$CH_2$); 7.15–7.35 (5H aromatic).

N-Butoxymethyl-N-trimethylsilylmethylbenzylamine may be prepared according to the method of Y. Terao et al., Chem. Pharm. Bull., 33, 2762 (1985).

4-Allyloxycarabony-5-methylcyclohex-2-enone may be prepared by analogy with the method described by P. E. Vorndam, J. Org. Chem., 55, 3693 (1990).

EXAMPLE 20

To a suspension, cooled to +5° C., of 0.5 g of (3aRS, 7RS,7aSR)-7-hydroxy-7-(2-methoxyphenyl)-2-[(2-methoxyphenyl)acetyl]-4-perhydroisoindolone in 50 cm³of methanol is added 0.027 g of sodium borohydride. After stirring for 2 hours at 5° C., 0.2 cm³ of 1N hydrochloric acid is added to the reaction solution which is then concentrated to dryness under reduced pressure. The residue is taken up in 50 cm³ of water and 70 cm³ of dichloromethane. After stirring, the suspension obtained is filtered and the organic phase of the filtrate is washed with water and then dried over magnesium sulphate and concentrated to dryness under reduced pressure (2.7 kPa). 0.42 g of (3aRS,4RS,7SR,7aSR)-4-(2-methoxyphenyl)-2-[(2-methoxyphenyl)acetyl]-4,7-perhydroisoindolediol is obtained in the form of a white foam.

Proton NMR spectrum (DMSO $d_6$ +$CH_3COOD$). 1.60 (mt, J=12.5, 8 and 4, 1H, H at 5); 1.70 (mt, J=14 and 8, 1H, H at 5); 2.05 (mt, J=14, 12.5 and 3, 1H, H at 6); 2.45 (mt, J=14 and 4, 1H, H at 5); 2.7 (mt, 1H, H at 7a); 3.0 (broad dd, J=7, 1H, H at 3a); 3.20 (cplx, 1H, H at 3); 3.45 (dd, J=12 and 1.5, 1H, H at 3); 3.58 (mt, 3H, H at 1 and $CH_2CO$); 3.75 (cplx, 1H, H at 1); 3.8 (s, 3H, $OCH_3$); 3.9 (s, 3H, $OCH_3$); 4.05 (mt, 1H, H at 7); 6.95–7.60 (m, 8H, aromatic).

Infra-red spectrum ($CH_2Cl_2$), characteristic bands (cm$^{-1}$): 3600+3530, 2975, 2880, 2835, 1630, 1600+1580+1495, 1465, 1440, 1245, 1060, 1030.

(3aRS,7RS,7aSR)-7-Hydroxy-7-(2-methoxyphenyl)-2-[ (2-methoxyphenyl)acetyl]-4-perhydroisoindolone may be prepared in the following way:

To a solution of 2.8 g of (3aRS,7RS,7aSR)-7-hydroxy-7-(2-methoxyphenyl)-4-perhydroisoindolone and 1.3 cm³ of triethylamine in 60 cm³ of anhydrous dichloromethane are added 1.55 g of (2-methoxyphenyl)acetic acid, 0.03 g of hydroxybenzotriazole hydrate and 1.96 g of 1-(3-dimethylaminopropyl)-3-ethylcarbodiimide hydrochloride. After stirring for 20 hours at 20° C., the reaction mixture is washed with 100 cm³ of water, dried over magnesium sulphate and then concentrated to dryness under reduced pressure (2.7 kPa). The residue obtained is recrystallized in ethyl ether and the crystals are drained and then dried under reduced pressure (2.7 kPa). 3.1 g of (3aRS,7RS,7aSR)-7-hydroxy-7-(2-methoxyphenyl)-2-[(2-methoxyphenyl) acetyl]-4-perhydroisoindolone are obtained, in the form of a white solid melting at 184° C.

(3aRS,7RS,7aSR)-7-Hydroxy-7-(2-methoxyphenyl)-4-perhydroisoindolone hydrochloride may be prepared by hydrogenation of a suspension of 3.3 g of (3aRS,7RS,7aSR) -2-benzyl-7-hydroxy-7-(2-methoxyphenyl)-4-perhydroisoindolone in 60 cm³ of methanol and 10 cm³ of 1N hydrochloric acid at atmospheric pressure for 24 hours at 20° C. in the presence of 0.6 g of 10% palladium hydroxide on charcoal. The reaction mixture is filtered and concentrated to dryness under reduced pressure (2.7 kPa). 2.8 g of (3aRS,7RS,7aSR)-7-hydroxy-7-(2-methoxyphenyl)-4-perhydroisoindolone hydrochloride are obtained in the form of foam.

Proton NMR spectrum (DMSO $d_6$+$CH_3COOD$): 2.90 (broad d, J=8, 2H at 1); 3.35 (mt, 3H, 2H at 3 and H at 3a or H at 7a); 3.8 (mt, J=8 and 10, 1H, H at 3a or H at 7a); 3.9 (s, 3H, $OCH_3$); 7.0–7.55 (m, 4H aromatic).

Infra-red spectrum (KBr), characteristic bands ($cm^{-1}$): 3400, 3000–2250, 1600+1580+1490, 1455+1440, 1240, 1055, 1025, 795+760.

(3aRS,7RS,7aSR)-2-Benzyl-7-hydroxy-7-(2-methoxyphenyl)-4-perhydroisoindolone may be prepared in the following way:

To a solution of 7 g of (3aRS,4RS,7aSR)-2-benzyl-7,7-dimethoxy -4-(2-methoxyphenyl)-4-perhydroisoindolol in 70 cm³ of dry dichloromethane are added 6.5 cm³ of triethylamine and 6.5 cm³ of trifluoroacetic acid. After stirring for 3 hours at room temperature, the reaction mixture, cooled to +5° C., is basified with 50 cm³ of 1N sodium hydroxide. The organic phase is separated out, washed with water, dried over magnesium sulphate and then concentrated to dryness under reduced pressure (2.7 kPa). The oil obtained is crystallized in diisopropyl ether. The solid, washed with petroleum ether, is then drained and dried under reduced pressure at 40° C. 3.4 g of (3aRS,7RS,7aSR) -2-benzyl-7-hydroxy -7-(2-methoxyphenyl)-4)-perhydroisoindolone are obtained, in the form of a cream-coloured solid. M.p.=96C.

(3aRS,4RS,7aSR)-2-Benzyl-7,7-dimethoxy-4-(2methoxyphenyl)-4-perhyddroisoindolol may be prepared according to the following experimental procedure:

To a suspension of 2-methoxyphenylmagnesium bromide (prepared from 19.3 cm³ of 2-bromoanisole and 3.7 g of magnesium) in 30 cm³ of dry ethyl ether are added, over 30 minutes, a solution of 18.1 g of (3aRS,7aSR)-2-benzyl-7,7-dimethoxy-4-perhydroisondolone in 100 cm³ of ethyl ether. The reaction mixture is subsequently brought to reflux for one hour and then diluted with 50 cm³ of tetrahydrofuran. After reflux for 3 hours and 20 hours at 0° C., the mixture is cooled to +5° C., treated with 100 cm³ of saturated aqueous ammonium chloride solution and extracted with 200 cm³ of ethyl acetate.

The organic phase is washed with water, dried over magnesium sulphate and concentrated to dryness under reduced pressure. The residue is purified by chromatography on a column of silica gel (particle size 0.06–0.20 mm) in a mixture of cyclohexane and ethyl acetate (80/20 by volume). After drying of the product under reduced pressure (15 Pa), 7 g of (3aRS,4RS,7aSR)-2-benzyl-7,7-dimethoxy-4-(2-methoxyphenyl)-4-perhydroisoindolol are obtained in the form of an oil.

Proton NMR spectrum ($C_6D_6$): 1.80 (mt, 2H, H at 5 and H at 6); 2.10 (dd, J=9 and 5, 1H, H at 1); 2.30 (dd, J=11.5 and 10, 1H, H at 3); 2.5 (mt, J=14 and 4, 1H, H at 5); 2.7 to 3.0 (mt, 3H, H at 6 and H at 1 and H at 3a or at 7a); 3.10 (s, 3H, $OCH_3$); 3.20 (s, 3H, $OCH_3$); 3.25 (mt, 2H, H at 3 and N—$CH_2$—Ph); 3.40 (mt, 2H, H at 7a and N—$CH_2$—Ph); 3.50 (s, 3H, $OCH_3$); 6.7–8.6 (m, H, aromatic).

Infra-red spectrum (KBr), characteristic bands ($cm^{-1}$): 3090+3070+3030, 2930, 2850, 2830, 2810 2730, 1600+ 1580+1485, 1370, 1465+1435, 1235, 1060, 1035, 700.

(3aRS,7aSR)-2-Benzyl-7,7-dimethoxy-4-perhydroisoindolone may be prepared by hydrogenation of a suspension of 19 g of (3aRS,7aSR)-2-benzyl-7,7-dimethoxy-2,3,3a, 4,7,7a-hexahydro-1H-4-isoindolone in 200 cm³ ethanol at atmospheric pressure and for 6 hours at 20° C. in the presence of Raney nickel (4 cm³ of filtered, commercial 50% aqueous suspension, washed times with 20 cm³ of ethanol). The reaction mixture is filtered and concentrated to dryness under reduced pressure (2.7 kPa). 18.1 g of (3aRS,7aSR)-2-benzyl-7,7-dimethoxy-4-perhydroisoindolone are obtained, in the form of a light-brown oil.

Proton NMR spectrum ($CDCl_3$): 3.18 (s, 3H, $OCH_3$); 3.2 (s, 3H, $OCH_3$); 3.6 (ab, J=12.5, 2H, N—$CH_2$—Ph); 7.30 (mt, 5H, phenyl).

Infra-red spectrum ($CCl_4$), characteristic bands ($cm^{-1}$): 3090+3070+3030, 2960, 2930, 2870, 2835, 2800+2730, 1740, 1715, 1495, 1470, 1455, 1245, 1030, 700.

(3aRS,7aSR)-2-Benzyl-7,7-dimethoxy-2,3,3a,4,7,7a-hexahydro-1H-4-isoindolone may be prepared in the following way:

To a solution of 22.9 g of 4,4-dimethoxy-2,5-cyclohexadien-1-one [J. Org. Chem., 52, 2763 (1987)] and 46 cm³ of N-butoxymethyl-N-trimethylsilylmethylbenzylamine in 150 cm³ of dry dichloromethane are added dropwise 3 cm³ of trifluoroacetic acid. Once the reaction mixture has reached reflux it is allowed to return to room temperature and is then stirred for for one hour. After addition of 5 g of potassium carbonate, the suspension obtained is filtered and the filtrate is concentrated to dryness under reduced pressure (2.7 kPa). The residue obtained is purified by chromatography on a column of silica gel (particle size 0.06–0.20 mm), eluting with a mixture of cyclohexane and ethyl acetate (90/10 then 80/20 by volume). 19 g of (3aRS,7aSR)-2-benzyl-7,7-dimethoxy-2,3, 3a, 4,7,7a -hexahydro-1H-4-isoindolone are obtained in oil form.

Proton NMR spectrum (DMSO $d_6$): 2.8 (mt, J=6.5 and 1.5, 1H, H at 7a or at 3a); 3.10 (mt, 1H, H at 7a or at 3a); 3.17 (s, 3H, $OCH_3$); 3.2 (s, 3H, $OCH_3$); 3.6 (ab, J=13.5, 2H, $NCH_2Ph$); 6.18 (d, J=9, 1H, H at 5); 6.9 (dd, J=9 and 2.5, 1H, H at 6); 7.3 (mt, 5H, aromatic).

Infra-red spectrum ($CCl_4$), characteristic bands ($cm^{-1}$): 3095+30710+3030, 2930, 2830, 2800+2740, 1690, 1645, 1495, 1455, 1380, 1235, 1045, 700.

EXAMPLE 21

To a suspension, cooled to −70° C. and under an argon atmosphere, of 0.5 g of (3aRS,7RS,7aSR)-7-hydroxy-7-(2-methoxyphenyl)-2-[(2-methoxyphenyl)acetyl ]-4-perhydroisoindolone are slowly added 4 cm³ of 1.6 M methyllithium solution in ethyl ether. After returning to room temperature and stirring for 3 hours, the reaction mixture is cooled to +5° C., followed by addition of 25 cm³ of saturated aqueous ammonium chloride solution and 20 cm³ of ethyl acetate. The organic phase is dried over magnesium sulphate and then concentrated to dryness under reduced pressure (2.7 kPa). The residue is chromatographed on a column of silica gel (particle size 0.06–0.20 mm) in ethyl acetate and then in a mixture of ethyl acetate and methanol (90/10 by volume). After drying under reduced pressure and recrystallization in acetonitrile, 0.1 g of (3aRS, 4RS,7aSR)-4-(2-methoxyphenyl)-2-[(2-methoxyphenyl) acetyl]-7-methyl-4,7-perhydroisoindolediol is obtained, in the form of white crystals melting at 180° C.

EXAMPLE 22

To a solution of 0.81 g of (3aRS,4RS,7aRS)7,7-dimethyl-4-(2-methoxyphenyl)-2-[(2-methoxyphenyl)acetyl]-2,3,3a, 4,4a-hexahydro-1H-4-isoindolol in 6 cm³ of pyridine is added 0.5 g of osmium tetroxide dissolved in 5 cm³ of pyridine. The reaction mixture is stirred at room temperature for 48 hours, followed by addition of a solution of 0.9 g of sodium bisulphite in 15 cm³ of water, and then 10 cm³ of pyridine; the mixture is decanted, washed three times with 10 cm³ of water and then with 10 cm³ of saturated aqueous sodium chloride solution. The organic phase is separated out after settling has taken place, dried over magnesium sulphate, filtered and concentrated to dryness under reduced pressure (2.7 kPa). The residue size chromatographed on a column of silica gel (particle size 0.04–0.06 mm, diameter 2 cm, height 20 cm), eluting under a pressure of 0.5 bar of nitrogen with a mixture of 1,2-dichloroethane and methanol (80/20 by volume) and collecting 25 cm³ fractions. Fractions 5 to 10 are combined and then concentrated to dryness under reduced pressure (2.5 kPa). The residue is triturated in diisopropyl ether. 0.169 g of (3aRS,4RS,7aRS)-7,7-dimethyl-4-(2-methoxyphenyl)-2-[(2-methoxyphenyl) acetyl]-4,5,6-perhydroisoindoletriol is obtained in the form of a white foam.

Proton NMR spectrum (DMSO $d_6$), two rotamers at room temperature:

1.2 (s, 6H, 2 CH₃); 2.23 (m, 1H, CH); 3.2 to 3.7 (m, 8H, CHOH +2 CH₂N +CH₂CO); 3.8 (s, 3H, OCH₃); 3.9 (s, 3H, OCH₃); 4.74 (d, 1H, CHOH); 6.9–7.63 (m, 8H, aromatic).

IR spectrum (KBr—characteristic bands in cm⁻¹): 3375, 3075, 2960, 2910, 2880, 2835, 1620, 1600–1495–1485, 1465–1440, 1250, 1085–1055, 1030, 755.

To a suspension of 22.73 g of 2-methoxyphenylmagnesium bromide in 70 cm³ of tetrahydrofuran, cooled to 15° C., are added, dropwise and with stirring, a solution of 6.77 g of (3aRS,7aRS)7, 7-dimethyl-2-[(2-methoxyphenyl)acetyl]-2,3,3a,4,7,7a -hexahydro-1H-4-isoindolone in 10 cm³ of tetrahydrofuran, followed by 5.3 g of anhydrous cerium chloride. The reaction mixture is stirred at room temperature for 18 hours, treated with 80 cm³ of saturated aqueous ammonium chloride solution, taken up in 100 cm³ of ethyl acetate and washed with 100 cm³ of saturated aqueous sodium chloride solution. The organic phase is separated out after settling has taken place, dried over magnesium sulphate, filtered and concentrated to dryness under reduced pressure (2.7 kPa). The residue is chromatographed on a column of silica gel (particle size 0.04–0.06 mm, diameter 5.5 cm, height 30 cm), eluting under a pressure of 0.5 bar of nitrogen with a mixture of cyclohexane and ethyl acetate (50/50 by volume) and collecting 75 cm³fractions. Fractions 17 to 40 are combined and then concentrated to dryness under reduced pressure (2.5 kPa). 4.98 g of (3aRS,4RS,7aRS)-7,7-dimethyl-4-(2-methoxyphenyl)-2-[(2-methoxyphenyl) acetyl]2,3,3a,4,7,7a-hexahydro-1H-4-isoindolol are obtained in the form of a colourless oil.

IR spectrum (KBr—characteristic bands in cm³¹):3500, 2945, 2885, 2855, 2840, 1640, 1600–1580 1495, 1465, 1245, 1025.

(3aRS,7aRS)-7,7-Dimethyl-2-[(2-methoxyphenyl)acetyl] -2,3,3a,4,7,7a-hexahydro-1H-4-isoindolone may be prepared in the following way:

By working according to the experimental procedure of Example 16, from 5.2 g of (3aRS,7aRS)-7,7-dimethyl-2-[ (2-methoxyphenyl)acetyl]-2,3,3a,4,7,7a -hexahydro-1H-4-isoindolone hydrochloride and 4.71 g of 2-methoxyphenylacetic acid and by adding 3.62 cm³ of triethylamine, and after purification on a column of silica gel (particle size 0.04–0.06 mm, diameter 6 cm, height 30 cm), 5.96 g of (3aRS,7aRS)-7,7-dimethyl-2-(2-methoxyhenyl) acetyl]-2,3,3a,4,7,7a-hexahydro-1H-4-isoindolone are obtained in the form of a colourless oil.

(3aRS,7aRS)-7,7-Dimethyl-2-[(2-methoxyphenyl)acetyl] -2,3,3a,4,7,7a-hexahydro-1H-4-isoindolone hydrochloride may be prepared in the following way:

A solution of 5.83 g of (3aRS,7aRS)-7,7-dimethyl-2-vinyloxycarbonyl-2,3,3a,4,7,7a-hexahydro-1H-4-isoindolone in 80 cm³ of hydrochloric acid-saturated dioxane is stirred at room temperature for 1 hour and then concentrated to dryness under reduced pressure (2.5 kPa). The residue is dissolved in 150 cm³ of ethanol and the solution is brought to reflux for 1 hour 30 minutes and is then concentrated to dryness under reduced pressure (2.5 kPa). 5.2 g of (3aRS,7aRS)7,7-dimethyl-2,3,3a,4,7,7a-hexahydro-1H-4-isoindolone hydrochloride are obtained in the form of a brown foam.

IR spectrum (KBr—characteristic bands in cm⁻¹): 2965, 2900, 2710–2490–2435, 1675, 1590, 1460, 1380–1370.

(3aRS,7aRS)-7,7-Dimethyl-2-vinyloxycarbonyl-2,3,3a,4, 7,7a-hexahydro-1H-4-isoindolone may be obtained in the following To a solution of of 14.7 g of (3aRS,7aRS)-2-benzyl-7,7-dimethyl-2,3,3a,4,7a-hexahydro-1H-4-insondolone in 100 cm³ of 1,2-dichloroethane are added, at room temperature, 7.9 cm³ of vinyl chloroformate. The reaction mixture is brought to reflux for 1 hour 30 minutes and then concentrated to dryness under reduced pressure (2.7 kPa). The residue is chromatographed on a column of Merck silica gel (particle size 0.04–0.06 mm, diameter 6.6 cm, height 30 cm), eluting under a pressure of 0.5 bar of nitrogen with a mixture of cyclohexane and ethyl acetate (80/20 by volume) and collecting 75 cm³ fractions. Fractions 56 to 70 are combined and then concentrated to dryness under reduced pressure (2.5 kPa). 5.83 g of (3aRS,7aRS)-7,7-dimethyl-2-vinyloxycarbonyl-2,3,3a,4,7,7a-hexahydro-1H-4-isoindolone are obtained in the form of a yellow oil.

(3aRS,7aRS)-2-Benzyl-7,7-dimethyl-2,3,3a,4,7,7a-hexahydro-1H-4-isoindolone may be prepared in the following way:

To a solution of 15.96 g of 4,4-dimethyl-2,5-cyclohexadienone and 46 cm³ of N-butoxymethyl-N-trimethylsilylmethylbenzylamine in 200 cm³ of dichloromethane are added, at a temperature of 10° C., 8 drops of trifluoroacetic acid. The reaction mixture is brought to reflux for 2 hours and potassium carbonate is then added and the solution is filtered through a sinter funnel and concentrated to dryness under reduced pressure (2.7 kPa). The residue is chromatographed on a column of silica gel (particle size 0.04–0.06 mm, diameter 8.5 cm, height 30 cm), eluting under a pressure of 0.5 bar of nitrogen with a mixture of cyclohexane and ethyl acetate (80/20 by volume) and collecting 100 cm³ fractions. Fractions 38 to 56 are combined and concentrated to dryness under reduced pressure (2.7 kPa). 14.7 g of (3aRS,7aRS)-2-benzyl-7,7-dimethyl-2,3,3a,4,7,7a-hexahydro-1H-4-isoindolone are obtained in the form of a yellow oil.

4,4-Dimethyl-2,5-cyclohexadienone is prepared according to the method of Zimmerman, J. Am. Chem. Soc., 93, 3653 (1971).

EXAMPLE 23

By working according to the experimental procedure of Example 22, from 2 g of (3aRS,4RS,7aRS)-7-methyl-7-phenyl-4-(2-methoxyphenyl)-2-[(2-methoxyphenyl)acetyl]-2,3,3a,4,7,7a-hexahydro-(1H)-4-isoindolol and 1 g of osmium tetroxide, and after purification on a column of silica gel, 0.6 g of (3aRS,4RS,7SR,7aRS)-7-methyl-7-phenyl-4-(2 -methoxyphenyl)-2-[(2-methoxyphenyl)acetyl] -4,5,6-perhydroisoindoletriol is obtained in the form of a beige-coloured foam.

Proton NMR spectrum (DMSO $d_6$ $_{+CH3}$COOD, 250 MHz, T=393° K., δ in ppm).

Diastereoisomer A: 1.44 (s, 3H, C$\underline{H}_3$); 2.70–3.80 (8H, CO—C$\underline{H}_2$Ph and C—C$\underline{H}$—CH$_2$N and N—C$\underline{H}_2$—CH); 3.70 (s, 3H, OC$\underline{H}_3$); 3.90 (s, 3H, OC$\underline{H}_3$), 4.53 (d, 1H, C$\underline{H}$—OH); 4.95 (d, 1H, CH—O$\underline{H}$); 6.75–7.75 (13H, aromatic).

Diastereoisomer B: 1.70 (s, 3H, C$\underline{H}_3$); 2.70–3.80 (8H, CO—C$\underline{H}_2$Ph and C—C$\underline{H}$—CH$_2$N and N—C$\underline{H}_2$—CH); 3.70 (s, 3H, OC$\underline{H}_3$); 3.95 (s, 3H, OC$\underline{H}_3$); 4.39 (d, 1H, C$\underline{H}$—OH); 4.90 (d, 1H, CH—O$\underline{H}$); 6.75–7.75 (13H, aromatic).

IR spectrum (CHCl$_3$, characteristic bands in cm$^{-1}$): 3450, 3105–3065, 2940, 2875, 2835, 1735, 1625, 1605–1495, 1465–1440, 1250–1240, 1030–1050, 700.

(3aRS,4RS,7S,7aRS)-7-Methyl-7-phenyl-4-(2-methoxyphenyl)-2-[(2-methoxyphenyl)acetyl]-2,3,3a,4,7,7a-hexahydro-(1H)-4-isoindolol may be prepared in the following way:

By working according to the experimental procedure of Example 22, from 3.75 g of (3aRS,7SR,7aRS)-7-methyl-7-phenyl-2-[(2-methoxyphenyl)acetyl]-2,3,3a,4,7,7a-hexahydro-1(H)-4-isoindolone, and after crystallization in a cyclohexane/ethyl acetate mixture (90/10 by volume), 2.1 g of (3aRS,4RS,7S,7aRS)-7-methyl-7-phenyl-4-(2-methoxyphenyl)-2-[(2-methoxyphenyl)acetyl]-2,3,3a,4,7,7a-hexahydro-(1H)-4-isoindolol are obtained, in the form of white crystals melting at 188° C.

(3aRS,7SR,7aRS)-7-Methyl-7-phenyl-2-[(2-methoxyphenyl)acetyl]-2,3,3a,4,7,7a-hexahydro-1(H)-4-isoindolone may be prepared in the following way:

By working according to the experimental procedure of Example 16, from 7 g of (3aRS,7SR,7aRS)-7-methyl-7-phenyl-2-[(2-methoxyphenyl)acetyl]-2,3,3a,4,7,7a-hexahydro-1(H)-4-isoindolone hydrochloride and 5.38 g of 2-methoxyphenylacetic acid, and after purification on a column of silica gel, 7.25 g of (3aRS,7SR,7aRS)-7-methyl-7-phenyl-2-[(2-methoxyphenyl)acetyl]-2,3,3a,4,7,7a-hexahydro-1(H)-4-isoindolone are obtained in the form of a yellow oil.

IR spectrum (CCl$_4$, characteristic bands in cm$^{-1}$): 3450, 3090–3065–3030, 2975, 2940, 2875, 2835, 1680, 1650, 1605–1495, 1460, 1440, 1245, 1050–1030, 700.

(3aRS,7SR,7aRS)-7-Methyl-7-phenyl-2-[(2-methoxyphenyl)acetyl]-2,3,3a,4,7,7a-hexahydro-1(H)-4-isoindolone hydrochloride may be prepared in the following way:

By working according to the experimental procedure of Example 22, from 8 g of (3aRS,7SR,7aRS)-7-methyl-7-phenyl-2-vinyloxycarbonyl-2,3,3a, 4,7,7a -hexahydro-1(H) -4-isoindolone, 7 g of (3aRS,7SR,7aRS)-7-methyl-7-phenyl-2-[(2-methoxyphenyl)acetyl]-2,3,3a, 4,7,7a-hexahydro-1(H)-4-isoindolone hydrochloride are obtained, in the form of a pink foam which is used directly in the following step.

(3aRS,7SR, 7aRS)-7-Methyl-7-phenyl-2-(vinyloxycarbonyl)-2,3,3a,4,7,7a-hexahydro-1(H)-4-isoindolone may be obtained in the following way:

To a solution of 11.7 g of (3aRS,7SR,7aRS)-2benzyl-7-methyl-7-phenyl-2,3,3a, 4,7,7a-hexahydro-1(H)-4-isoindolone in 150 cm$^3$ of 1,2-dichloroethane are added, at room temperature, 5.2 cm$^3$ of vinyl chloroformate. The reaction mixture is brought to reflux for 2 hours and then concentrated to dryness under reduced pressure (2.7 kPa). The residue is chromatographed on a column of silica gel (particle size 0.04–0.06 mm, diameter 4.5 cm, height 25 cm), eluting under a pressure of 0.5 bar of nitrogen with a mixture of cyclohexane and ethyl acetate (80/20 by volume) and collecting 90 cm$^3$ fractions. Fractions 10 to 21 are combined and then concentrated to dryness under reduced pressure (2.5 kPa). 8.1 g of (3aRS,7SR,7aRS)-7-methyl-7-phenyl-2-vinyloxycarbonyl-2,3,3a,4,7,7a-hexahydro-1(H)-4-isoindolone are obtained, in the form of a pale yellow oil which is used directly for the following step.

Proton NMR spectrum (DMSO $d_6$, 250 MHz, δ in ppm): 1.67 (s, 3H, C$\underline{H}_3$); 2.60 (m, 2H, N—C$\underline{H}_2$—CH); 3.10 (m, 1H, CH$_2$—C$\underline{H}$—C); 3.30 (m, 2H, N—C$\underline{H}_2$—CH), 3.40 (m, 1H, CH$_2$—CH—C); 4.00 (d, 1H, CO—C$\underline{H}$=CH$_2$); 4.40 and 4.7 (2d, 2×1H, —CH=C$\underline{H}$hd 2); 6.11 (d, 1H, CH=C$\underline{H}$—C); 6.95 (q, 1H, CO—C$\underline{H}$=CH$_2$); 7.2–7.5 (m, 5H, aromatic).

CO—C$\underline{H}$=CH$_2$); 7.2–7.5 (m, 5H, aromatic).

2,3,3a,4,7,7a-hexahydro-1(H)-4-isoindolone may be obtained in the following way:

By working according to the experimental procedure of Example 22, from 11.8 g of (4RS)-4-phenyl-4-methyl-2,5-cyclohexadien-1-one and 28 cm$^3$ of N-butoxymethyl-N-trimethylslylmethylbenzylamine, and after chromatography on a column of silica gel and crystallization in isopropyl ether, 6 g of (3aRS,7SR,7aRS)-2-benzyl-7-methyl-7-phenyl-2,3,3a,4,7,7a-hexahydro-1(H)-4-–isoindolone are obtained, in the form of a yellow solid melting at 110° C.

4-Phenyl-4-methyl-2,5-cyclohexadienone may be prepared according to the method of H. E. Zimmerman and G. Jones, J. Amer. Chem. Soc., 92, 9, 2753 (1970).

EXAMPLE 24

To a solution of 1.0 g of (3aS,4S,6R,7aR)-4-(2-methoxyphenyl)-6-methyl-4-perhydroisoindolol in 100 cm$^3$ of dichloromethane are added 1.5 cm$^3$ of triethylamine. The reaction mixture is cooled to 5° C. and 0.60 g of (2-dimethylaminophenyl)acetic acid, 0.10 g of 1-hydroxybenzotriazole monohydrate and 0.70 g of 1-(3-dimethylaminopropyl)-3-ethylcarbodiimide hydrochloride are added. The reaction mixture is maintained at 5° C. for 1 hour and at 20° C. for 16 hours and is then washed twice with 100 cm$^3$ of water, dried over magnesium sulphate, filtered and concentrated under reduced pressure (2.7 kPa). The residue is chromatographed on a column of silica gel (0.060–0.200 mm, diameter 4 cm, height 50 cm), eluting under a pressure of 0.7 bar with a mixture of dichloromethane and methanol (97/3 by volume) and collecting 50 cm$^3$ fractions. Fractions 14 to 19 are concentrated and, after drying at 40° C. and at 15 Pa, 1.0 g of (3aS,4S,6R,7aR)-4-(2-methoxyphenyl)-2-[(2-dimethylaminophenyl)acetyl]-6-methyl-4-perhydroisonindolol is obtained, in the form of a white powder which is dissolved in 50 cm³ of dioxane. 3 cm³ of 5M hydrochloric acid solution are added to the dioxane and, after 1 hour at room temperature, the solution is concentrated under reduced pressure (2.7 kPa), stirred in isopropyl ether, filtered and dried at 40° C. under 15 Pa. 0.94 g of (3aS,4S,6R,7aR)-4-(2-methoxyphenyl)-2-[(2-dimethylaminophenyl)acetyl]-6-methyl-4-perhydroisoindolol hydrochloride is obtained.

¹H NMR spectrum (250 MHz, (CD$_3$)$_2$SO d$_6$ with addition of a few drops of CD$_3$COOD d$_4$, δ in ppm): at room temperature, a mixture of the rotamers is observed. 0.91 and 0.92 (2d, J=7 Hz, 3H in total: CH$_3$ at 5); from 1.25 to 1.90 (mt, 3H: CH$_2$ 7 and 1H of the C$_2$ 5); from 2.00 to 2.50 (mt, 2H: the other H of the CH$_2$ 5 and H 6); from 2.50 to 2.80 (mt, 1H: H 7a); 2.83 and 3.00 (2t broad, J=8 Hz, 1H in total: H 3a); 3.00 to 4.20 (mt, 6H: NCH$_2$ 1–NCH$_2$ 3 and CH$_2$Ar); 3.24 (s, 6H: N(CH$_3$)$_2$); 3.80 and 3,.83 (2s, 3H in total: OCH$_3$); from 6.85 to 7.95 (mt, 8H: aromatic H).

IR: (KBr, cm⁻¹): 3420, 2950–2920, 2790–2100, 1640, 1600, 1500, 1435, 1465, 1375, 1235, 1025, 760.

$[\alpha]^D_{20}$=19.5° (c=5 g/l methanol.

2-Dimethylaminophenylacetic acid may be prepared according to the method described in Patent EP 429,366.

(3aS,4S,6R,7aR)-4-(2-Methoxyphenyl)-6-methyl-4-perhydroisoindolol may be prepared as in Example 1, starting from (R)-5-methylcyclohex-2-enone, the preparation of which is described by W. Oppolzer and M. Petrzilka, Helv. Chim. Acta, .61(8) 2755 (1978).

EXAMPLE 25

To a solution of 1.0 g of (3aS,4S, 6R,7aR)-4-(2-methoxyphenyl)-6-methyl-4-perhydroisoindolol in 70 cm³ of dichloromethane is added 1.0 cm³ of triethylamine. The reaction mixture is cooled to 5° C. and 0.69 g of 2-(S)-(2-benzoxyphenyl)propionic acid, 0.045 g of 1-hydroxybenzotriazole monohydrate and 0.56 g of 1-(3-dimethylaminopropyl)-3-ethylcarbodiimide hydrochloride are added. The reaction mixture is maintained at 5° C. for 1 hour and at 20° C. for 16 hours and is then washed twice with 50 cm³ of water, dried over magnesium sulphate, filtered and concentrated under reduced pressure (2.7 kPa). The residue is chromatographed on a column of silica gel (0.060–0.200 mm, diameter 4 cm, height 35 cm), eluting under a pressure of 0.7 bar with a mixture of dichloromethane and methanol (97.5/2.5 by volume) and collecting 25 cm³ fractions. Fractions 8 to 14 are concentrated and, after drying at 40° C. and at 15 Pa, 1.0 g of (3aS,4S,6R,7aR)-4-(2-methoxyphenyl)-2-[2-(S)-2-benzoxyphenyl)propionyl]-6-methyl-4-perhydroisoindolol is obtained, in the form of a white solid.

¹H NMR spectrum (250 MHz, (CD$_3$)-$_2$SO d$_6$ with addition of a few drops of CD$_3$COOD d$_4$, at a temperature of 393 K., a in ppm): 0.91 (d, J=7 Hz, 3H: CH$_3$ at 5); from 1.25 to 1.40 and 1.72 (2 mts 1H-each: CH$_2$ 7); 1.30 (d, J=7 Hz, 3H: CH$_3$ 5); 1.62 and 2.05 (broad d and, respectively, t; J=12.5 Hz, 1H each: CH$_2$ 5); 2.17 (mt, 1H: H 6); 2.37 (mt, 1H: H 7a); 2.77 (broad t, J=7.5 Hz, 1H: H 3a); from 3.05 to 3.60 (mt, 4 H: NCH$_2$1 and NCH$_2$ 3); 3.83 (s, 3H: OCH$_3$); 419 (q, J=7 Hz, 1H: CHAr); from 4.95 to 5.25 (mt, 2H: OCH$_2$Ar); from 6.85 to 7.55 (mt, 13H: aromatic H).

IR (KBr, cm⁻¹): 3425, 3075, 2950, 2925, 2870, 2850, 1635, 1600, 1585, 1490, 1455, 1435, 1235, 1030, 755, 700.

To a solution of 0.85 g of (3aS,4S, 6R, 7aR)-2-[2-(S)-(2-benzoxyphenyl) propionyl]-4-(2-methoxyphenyl)-6-methyl-4-perhydroisoindolol in 12 cm³ of absolute ethanol is added 0.2 g of 20% palladium hydroxide on charcoal, and hydrogen is sparged through the reaction mixture at 40° C. for 3 hours. After returning to room temperature and flushing with argon, the mixture is filtered over fire and concentrated to dryness under reduced pressure (2.7 kPa). The residue is recrystallized in ethanol and, after filtration and drying, 0.5 g of (3aS,4S,6R,7aR)-2-(S)-(2-hydroxyphenyl) propionyl]-4-(2-methoxtphenyl)-6-methyl-4-perhydroisoindolol is obtained, in the form of white crystals melting at 280° C.; $[\alpha]_D$=–26.5° (c=5.3 g/l , CHCl$_3$).

2-(S)-(2-Benzoxyphenyl)propionic acid may be prepared according to the method described in Patent Application WO 93/21155.

EXAMPLE 26

By working in an identical manner to Example 1, 1.5 g of (3aRS,4RS,7SR,7aRS)-7-(hydroxymethyl)-4-(2-methoxphenyl)-7-methyl-4-perhydroisoindolol and 0.9 g of (2-N,N-dimethylinophenyl)acetic acid are used. After concentration, the crude residue is recrystallized in acetonitrile and, alter drying at 40° C. and at 15 Pa, 1.0 g of (3aRS,4RS,7SR,7aRS)-2-[(2-N,N-dimethylaminophenyl) acetyl]-7-(hydroxymethyl)-4-(2-methoxyphenyl)-7-methyl-4-perhydroisoindolol is obtained, in the form of a white solid melting at 138°–142° C.

EXAMPLE 27

By working in an identical manner to Example 1, 3.0 g of (3aRS,4RS,7SR,7aRS)-7-(hydroxymethyl)-4-(2-methoxyphenyl)-7-methyl-4-perhydrosoindolol and 1.74 g of (S)-2-(2-methoxyphenyl)propionic acid are used. After recrystallization of the crude residue in acetonitrile, the 2 diastereoisomers are separated by High Performance Liquid Chromatography (HPLC) on a column of silica gel (diameter 4 cm, height 10 cm), eluting with a mixture of ethyl acetate, cyclohexane and methanol (64/35/1 by volume). The fractions collected are concentrated, the solid is recrystallized in acetonitrile and, after drying at 40° C. and at 15 Pa, 0.10 g of (3aS,4S,7R,7aS)-7-(hydroxymethyl)-4-(2-methoxyphenyl)-2-[2-(S)-(2-methoxyphenyl)propionyl]-7-methyl-4-perhydroisondolol is obtained, in the form of white crystals melting at 215° C.

EXAMPLE 28

By working as in Example 1 and after HPLC separation, (3aS,4S,6R,7aR)-2-[2-(S)-(2-N,N-dimethylaminophenyl) propionyl]-4-(2-methoxyphenyl)-6-methyl-4-perhydroisoindolol is obtained, in the form of a white solid melting at 83° C. $[\alpha]^{20}{}_D$=+32.7° in methanol at 20° C. (c=5.08 g/l).

¹H NMR spectrum (250 MHz, (CD$_3$)$_2$SO d$_6$ with addition of a few drops of CD$_3$COOD d$_4$, at a temperature of 403 K., δ in ppm): 0.92 (d, J=7 Hz, 3H: CH$_3$ at 5); from 1.25 to 1.45 and 1.80 (mt and broad d respectively, J=14 Hz, 1H each: CH$_2$ 7); 1.36 (d, J=7 Hz, 3H: CH$_3$); 1.63 and 1.97 (broad d and, respectively, t; J=12.5 Hz, 1H each: CH$_2$ 5); 2.19 (mt, 1H: H 6); 2.48 (mt, 1H: H 7a); 2.58 (s, 6H: N(CH$_3$)$_2$; 2.82 (broad t, J=8 Hz, 1H: H 3a); from 3.10 to 3.60 (mt, 4H: NCH$_2$ 1 and NCH$_2$ 3); 3.83 (s, 3H: OCH$_3$); 4.46 (q, J=7 Hz, 1H: CHAr); from 6.85 to 7.40 (mt, 8H: aromatic H).

IR (KBr, cm⁻¹): 3420, 2925, 2870, 2780, 1625, 600, 1585, 1490, 1435, 1455, 1370, 1235, 1035, 755.

EXAMPLE 29

To a solution of 2.77 g of (3aRS,4RS,6SR,7aSR)-6-hydroxymethyl-4-(2-methoxyphenyl)-4-perhydroisoindolol, 1.80 g of 2-(S)-(2-methoxyphenyl) propionic acid and 30 mg of hydroxybenzotriazole hydrate in 80 cm³ of dichloromethane are added 2.1 g of 1-(3-dimethylaminopropyl)-3-ethylcarbodiimide. After stirring for 20 hours at 20° C., the reaction mixture is washed with 40 cm³ of water, dried over magnesium sulphate and concentrated to dryness under reduced pressure (2.7 kPa). The residue is chromatographed on a column of silica gel (particle size 0.06–0.20 mm, diameter 5 cm, height 40 cm) in a mixture of cyclohexane and ethyl acetate (30/70 by volume) and then in a mixture of ethyl acetate and methanol (90/10 by volume). 3.6 g of 6-hydroxymethyl-4-(2-methoxyphenyl)-2-[2-(S)-(2-methoxyphenyl)propionyl]-4-perhydroisoindolol (mixture of the two 3aR, 4R,6S,7aS,S and 3aS,4S,6R,7aRS diastereoisomers) are obtained after evaporation of the eluent and drying under reduced pressure (2.7 kPa), in the form of a white solid M.p.$_K$=178° C.

Proton NMR (DMSO d$_6$ with addition of a few drops of CD$_3$COOD, at a temperature of 393° K., $\delta$ in ppm): a mixture of the 2 diastereoisomers is observed. 1.20 to 2.10 (mt, 4H, CH$_2$ at 7 and CH$_2$ at 5); 1.29 and 1.33 (2d, J=7, 3H, CH$_3$); 2.05 to 2.30 (mt, 1H: H 6); 2.40 to 2.60 (mt, 1H: H 7a); 2.75 to 2.90 (mt, 1H, H: 3a); 2.90 to 3.60 (mt, 4H: NCH$_2$); 3.35 (d, J=5.5, 2H: OCH$_2$); 3.76–3.78–3.83 and 3.85 (4s, 6H: OCH$_3$); 4.05 to 4.25 (mt, 1H: ArCH); 6.85 to 7.65 (mt, 8H: aromatic H).

Infra-red spectrum (characteristic bands in cm$^{-1}$): 3425, 2930, 2885, 2840, 1625, 1600+1490 +1435, 1460, 1375, 1240, 1030, 755.

EXAMPLE 30

By working according to the experimental procedure of Example 16, from 1.21 g of 3-indoleacetic acid and 1.39 g of (3aRS,4RS,5RS,7aSR)-4-(2-methoxyphenyl)-5-methyl-4-perhydroisoindolol, and after purification on a column of silica gel (particle size 0.04–0.06 mm, diameter 2.8 cm, height 25 cm), eluting under a pressure of 0.5 bar of nitrogen with a mixture of cyclohexane and ethyl acetate (40/60 by volume), 0.88 g of (3aRS,4RS,5RS,7aSR)-4-(2-methoxyphenyl)-2-(3-indolylacetyl)-5-methyl-4-perhydroisoindolol is obtained in the form of a white foam.

Proton NMR spectrum (DMSO d$_6$, 250 MHz at a temperature of 393 K., d in ppm): 0.60 (d, J=7 Hz, 3H: CH$_3$); 1.36 and from 1.70 to 1.95 (2 mts, 1H and 3H respectively: CH$_2$ at 6 and CH$_2$ at 7); from 2.45 to 2.65 (mt, 2H: H 7a and H 5); 2.90 (t, J=7 Hz, 1H: H 3a); from 3.10 to 3.60 (mt, 4H: NCH$_2$ 3 and NCH$_2$ 1); 3.65 (broad s, 2H: ArCH$_2$); 3.75 (broad s, 1H: OH); 3.85 (s, 3H: OCH$_3$); from 6.90 to 7.65 (mt, 9H: aromatic H); 10.35 (cplx, 1H: NH).

EXAMPLE 31

By working as in Example 33, but starting with 2.5 g of (3aS,4S,6R,7aR)-4-(2-fluorophenyl)-6-methyl-4-perhydroisoindolol and 2.17 g of 2-(S)-(2-methoxyphenyl) propionic acid, and after purification on a column of silica gel (particle size 0.04–0.06 mm, diameter 4 cm, height 25 cm), eluting under a pressure of 0.5 bar of nitrogen with a mixture of cyclohexane and ethyl acetate (90/10 by volume), 3.87 g of a solid are obtained, which solid is recrystallized in acetonitrile to give 2 g of (3aS,4S,6R,7aR)-4-(2-fluorophenyl)-2-[2-(S)-(2-methoxyphenyl) propionyl]-6-methyl-4-perhydroisoindolol, in the form of a white solid melting at 170° C.

EXAMPLE 32

By working in an identical manner to Example 1, 1.5 g of (3aRS,4RS,7SR,7aRS)-7-(hydroxymethyl)-4-(2-methoxyphenyl)-7-methyl-4-perhydroisoindolol and 0.88 g of 3-indoleacetic acid are used. After concentration, the crude residue is recrystallized in acetonitrile and, after drying at 40° C. and 15 Pa, 0.7 g of (3aRS,4RS,7SR,7aRS) -7-(hydroxymethyl)-2-(3-indolylacetyl)-4-(2-methoxyphenyl)-7-methyl-4ethyl)-4-(2-methoxyphenyl)-7-methyl-4-perhydroisoindolol is obtained, in the form of a white solid melting at 170–180° C. (pasty melt).

$^1$H NMR spectrum (250 MHz, (CD$_3$)-2SO d$_6$ with addition of a few drops of CD$_3$COOD d$_4$, at a temperature of 393 K., $\delta$ in ppm): 1.12 and 1.48 (2 broad d, J=13 Hz, 1H each: 1H of the CH$_2$ 6 and 1H of the CH$_2$ 7); 1.23 (s, 3H: CH$_3$); 1.91 and 2.71 (2 broad dts, J=and 4 Hz, 1H each: the other H of the CH$_2$ 6 and the other H of the CH$_2$ 7); 2.18 (mt, 1H: H 7a); 3.02 (mt, 1H: H 3a); 3.25 and 3.33 (2d, J=10.5 Hz, 1H each: OCH$_2$ ); from 3.20 to 3.80 (mt, 4H: NCH$_2$ 3 and NCH$_2$ 1 ); 3.63 (broad s, 2H: ArCH$_2$ ) : 3.86 (s, 3H: OCH$_3$ ); from 6.90 to 7.65 (mt, 9H: aromatic H).

IR (KBr, cm$^{-1}$): 3420, 2925, 2875, 2830, 1610, 1485, 1435, 1460, 1230, 1025, 760, 740.

EXAMPLE 33

To a solution of 0.52 g of (3aRS,4RS,7aSR)-4-(3,5-bistrifluoromethylphenyl)-4-perhydroisoindolol and 0.34 g of 2-(S)-(2-methoxyphenyl)propionic acid in 10 cm³ of dichloromethane, cooled to 0° C., are added 0.02 g of 1-hydroxybenzotriazole and 0.37 g of 1-(3-dimethylaminopropyl)-3-ethylcarbodiimide hydrochloride. The mixture is stirred for 18 hours at room temperature and the organic phase is then washed with twice 20 cm³ of water, then with 20 cm³ of saturated aqueous sodium chloride solution, dried over magnesium sulphate and concentrated to dryness under reduced pressure (2.7 kPa). The residue is chromatographed on a column of silica gel (particle size 0.04–0.06 mm, diameter 2.6 cm, height 20 cm), eluting under a pressure of 0.5 bar of nitrogen with a mixture of cyclohexane and ethyl acetate (80/20 by volume) and collecting 20 cm³ fractions. Fractions 14 to 35 are combined and then concentrated to dryness under reduced pressure (2.7 kPa). 0.53 g of (3aR,4R,7aS)- and (3aS,4S,7aR)-2-[2-(S)-(2-methoxyphenyl)propionyl]-4-3,5-bis (trifluoromethyl)phenyl-4-perhydroisoindolol (50/50 mixture of the two diastereoisomers) is obtained, in the form of an off-white foam.

Proton NMR spectrum (DMSO d$_6$, 250 MHz, at a temperature of 393 K., a mixture of the two diastereoisomers is observed): from 1.20 to 2.0 (mt, 6H, CH$_2$); from 1.25 to 1.4 (mt, 3H, CH$_3$); from 2.3 to 2.7 (mt, 1H, H 7a); from 2.6 to 2.9 (mt, 1H, H 3a); from 3.1 to 3.65 (mt, 4H, NCH$_2$); 3.8 (very broad s, 3H, OCH$_3$); from 4.1 to 4.25 (mt, 1H, ArCH); from 4.8 to 5.2 (wide cplx, 1H, OH); from 6.95 to 7.4 (mt, 4H, H of the disubstituted aromatic); from 7.9 to 8.3 (mt, 3H, H of the trisubstituted aromatic).

Infra-red spectrum (characteristic bands in cm$^{-1}$): 3340, 2935, 2875, 2860, 1625, 1495, 1460, 1450, 1440, 1175, 1130, 845.

(3aRS,4RS,7aSR)-4-[3,5-bis(Trifluoromethyl)phenyl]-4-perhydroisoindolol may be obtained in the following way:

To a solution of 0.82 g of (3aRS,4RS,7aSR)-2 benzyl-[3,5-bis(trifluoromethyl)phenyl]-4-perhydroisoindolol in 15 cm³ of absolute ethanol is added 0.25 g of 10% palladium hydroxide on charcoal and the reaction mixture is then hydrogenated at reflux with stirring. After reaction for 1 hour, the reaction mixture is filtered and then concentrated to dryness under reduced pressure (2.7 kPa). 0.52 g of (3aRS,4RS,7aSR)-4-[3,5-bis(trifluoromethyl)phenyl]-4perhydroisoindolol is obtained in the form of a black paste.

(3aRS,4RS,7aSR)-2-Benzyl-[3,5-bis(trifluoromethyl) phenyl]-4-perhydroisoindolol may be obtained in the following way:

To a solution of 3.06 cm$^3$ of 3,5bis(trifluoromethyl) bromobenzene in 15 cm$^3$ of dry tetrahydrofuran is added, at −78° C., a solution of 10.9 cm$^3$ of 1.6M butyllithium in hexane. This solution is stirred for 30 minutes at −78° C., and a solution of 1 g of (3aRS,7aSR)-2-benzyl-4-perhydroisoindolone in 5 cm$^3$ of tetrahydrofuran is then run in dropwise. The reaction mixture is subsequently stirred at room temperature for 18 hours, treated with 20 cm$^3$ of water and then extracted with 20 cm$^3$ of ethyl acetate. The organic phase is separated out after settling has taken place, washed with twice 20 cm$^3$ of water, then with 20 cm$^3$ of saturated sodium chloride solution, dried over magnesium sulphate and concentrated to dryness under reduced pressure (2.7 kPa). The residue is chromatographed on a column of silica gel (particle size 0.04–0.06 mm, diameter 2 cm, height 20 cm), eluting under a pressure of 0.5 bar of nitrogen with a mixture of cyclohexane and ethyl acetate (90/10 by volume) and collecting 20 cm$^3$ fractions. Fractions 26 to 37 are combined and then concentrated to dryness under reduced pressure (2.7 kPa). 0.82 g of (3aRS,4RS,7aSR)-2-benzyl-4-[3,5-bis(trifluoromethyl)phenyl]-4-perhydroisoindolol is obtained in the form of an oil.

EXAMPLE 34

To a solution of 0.66 g of 2-methoxyphenylacetic acid in 30 cm$^3$ of dichloromethane is added, at 5° C., 0.65 g of N,N'-carbonyldiimidazole. After stirring for 4 hours at room temperature, a solution containing 1 g of (3aRS,4RS,5RS, 7SR,7aRS)-7- methyl-7-phenyl-4-(2-methoxyphenyl)-4,5-perhydroisoindolediol in 20 cm$^3$ of dichloromethane is added dropwise. After stirring for 48 hours, the reaction medium is washed with 50 cm$^3$ of water and then with 50 cm$^3$ of saturated aqueous sodium chloride solution. The organic phase is separated out after settling has taken place, dried over magnesium sulphate, filtered and concentrated to dryness under reduced pressure (2.7 kPa). The residue is chromatographed on a column of Merck silica gel (particle size 0.04–0.06 mm, diameter 2.2 cm, height 26 cm), eluting under a pressure of 0.5 bar of nitrogen with a mixture of cyclohexane and ethyl acetate (50/50 by volume) and collecting 35 cm$^3$ fractions. Fractions 11 to 25 are combined and then concentrated to dryness under reduced pressure (2.5 kPa). 1 g of (3aRS,4RS,5Rs,7SR,7aRS)-7-methyl-7-phenyl-4-(2-methoxyphenyl)-2-[(2-methoxyphenyl)acetyl]-4,5-perhydroisoindolediol is obtained in the form of a white foam.

$^1$H NMR (DMSO d$_6$+AcOD, 250 MHz, T=413 K., d in ppm): 1.60 (s, 3H: —CH$_3$); 1.85 and 2.45 (dd and t, 2×1H, CH—CH$_2$—C); 2.73 (m, 1H: C—CH$_2$N); 2.90 and 3.20 (2t, 2×1H, N—CH$_2$—CH); 3.20 and 3.50 (2m, 2×H, N—C H$_2$—CH); 3.22 (m, 1H: C—CH—CH$_2$—N); 3.38 (s, 2H, CO—CH$_2$—Ph); 3.68 (s, 3H, —OCH$_3$); 3.82 (s, 3H, OC H$_3$); 4.93 (dd, 1H, C—CH—OH); 6.80–7.65 (m, 13H, aromatic).

(3aRS,4RS,5RS,7SR,7aRS)-7-Methyl-7-phenyl-4 -(2-methoxyphenyl)-4,5-perhydroisoindolediol may be prepared in the following way:

To a solution of 1.6 g of (3aRS,4RS,5RS,7SR,7aRS)-2-benzyl-7-methyl-7-phenyl-4-(2-methoxyphenyl)-4,5-perhydroisoindolediol in 50 cm$^3$ of anhydrous ethanol is added 0.3 g of 20% palladium hydroxide on charcoal; the reaction mixture is then hydrogenated, with stirring, at a temperature of 60° C. and at atmospheric pressure. After reaction for 2 hours, the reaction mixture is filtered and then concentrated to dryness under reduced pressure (2.7 kPa). 1 g of (3aRS,4RS,5RS,7SR,7aRS), 7-methyl-7 phenyl-4-(2-methoxyphenyl)-4,5-perhydroisoindoledio is obtained, in the form of a cream-coloured foam which is used directly for the following step.

(3aRS,4RS,5RS,7SR,7aRS)-2-Benzyl-7-methyl-7-phenyl-4-(2-methoxyphenyl)-4,5-perhydroisoindolediol may be prepared in the following way:

37 cm$^3$ of 1.38 molar 2-methoxyphenylmagnesium bromide solution in tetrahydrofuran are added to a solution containing 2.4 g of (3aRS,5RS,7SR,7aRS)-5-acetoxy-2-benzyl-7-methyl-7-phenyl-4-perhydroisoindolone in 50 cm$^3$ of tetrahydrofuran at 4° C. The reaction mixture is stirred at room temperature for 18 hours, treated with 150 cm$^3$ of saturated aqueous ammonium chloride solution, taken up in 100 cm$^3$ of ethyl acetate and washed with 100 cm$^3$ of water and then with 100 cm$^3$ of saturated aqueous sodium chloride solution. The organic phase is separated out after settling has taken place, dried over magnesium sulphate, filtered and concentrated to dryness under reduced pressure (2.7 kPa). The residue is chromatographed on a column of Merck silica gel (particle size 0.04–0.06 mm, diameter 4 cm, height 27 cm), eluting under a pressure of 0.5 bar of nitrogen with a mixture of cyclohexane and ethyl acetate (60/40 by volume) and collecting 35 cm$^3$ fractions. Fractions 8 to 15 are combined and then concentrated to dryness under reduced pressure (2.5 kPa). 1.65 g of (3aRS,4RS,5RS,7SR,7aRS)-2-benzyl-7-methyl-7-phenyl-4 -(2-methoxyphenyl)-4,5-perhydroisoindolediol are obtained in the form of a yellow foam.

By working according to the experimental procedure of Example 15, from 16.22 g of 6-acetoxy-4-methyl-4-phenylcyclohex-2-enone (mixture of the A and B forms) and 22.25 g of N-butoxymethyl-N-trimethylsilylmethylbenzylamine, and after purification on a column of silica gel, 2 g of (3aRS,5RS,7SR,7aRS)-5-acetoxy-2-benzyl-7-methyl-7-phenyl-4-(2 -methoxyphenyl)-4-perhydroisoindolone are obtained in the form of a yellow oil.

$^1$H NMR (CDCl$_3$, 250 MHz, δ in ppm): 1.75 (s, 3H: —C H$_3$); 2.07 and 2.30 (t and dd, 2×1H, N—CH$_2$—CH); 2.25 (s, 3H, —CH$_3$); 2.44 and 2.60 (m and t, 2H, C—CH$_2$—CH); 2.77 and 3.48 (dd, 2H, N—CH$_2$—CH); 3.08 (t, 1H, CO—C H—CH); 3.19 (m, 1H, C—CH—CH); 3.53 and 3.53 and 3.63 (d, 2H, N—CH$_2$—Ph); 5.64 (dd, 1H, O—CH—CO); 7.15–7.40 (m, 5H, aromatic).

6-Acetoxy-4-methyl-4-phenylcyclohex-2-enone (6/4 mixture of the A and B forms) may be prepared from 4-methyl-4-phenylcyclohex-2-enone according to the method described by G. M. Rubottom et al., J. Org. Chem., 43, 1599, (1978).

4-Methyl-4-phenylcyclohex -2-enone may be prepared according to the method of H. E. Zimmerman and G. Jones, J. Am. Chem. Soc., 92, 9, 2753, (1970).

The present invention also relates to the pharmaceutical compositions consisting of a product of general formula (I) or a salt when they exist, optionally in combination with any other pharmaceutically compatible product, which may be inert or physiologically active. The compositions according to the invention may be used via the parenteral, oral, sublingual, rectal, topical, ocular or intranasal route or as aerosols for the lungs.

The sterile compositions for parenteral administration which may in particular be used in the form of infusions are preferably aqueous or non-aqueous solutions, suspensions or emulsions. Water, propylene glycol, a polyethylene glycol, vegetable oils, in particular olive oil, injectable organic esters, for example ethyl oleate, or other suitable organic solvents may be used as solvent or vehicle. These compositions may also contain adjuvants, in particular wetting, tonicity, emulsifying, dispersing and stabilizing agents. The sterilization may be achieved in several ways, for example by aseptic filtration, by incorporating sterilizing agents into the composition, by irradiation or by heating. They may also be prepared in the form of sterile solid compositions which may be dissolved at the time of use in an injectable sterile medium.

The compositions for rectal administration are suppositories or rectal capsules, which contain, besides the active product, excipients such as cocoa butter, semi-synthetic glycerides or polyethylene glycols.

Tablets, pills, powders or granules may be used as solid compositions for oral administration. In these compositions, the active product according to the invention (optionally combined with another pharmaceutically compatible product) is mixed with one or more inert adjuvants or diluents, such as sucrose, lactose or starch. These compositions may also contain substances other than diluents, for example a lubricating agent such as magnesium stearate.

Pharmaceutically acceptable emulsions, solutions, suspensions, syrups and elixirs containing inert diluents such as water or paraffin oil may be used as liquid compositions for oral administration. These compositions may also contain substances other than diluents, for example wetting, sweetening or flavouring products.

The compositions for topical administration may, for example, be creams, ointments or lotions.

The compositions for ocular administration may be instillations.

The compositions for intranasal administration may be pharmaceutically acceptable powders or solutions which are intended for drops or for sprays.

The compositions may also be aerosols. For use in the form of liquid aerosols, the compositions may be stable sterile solutions or solid compositions which are dissolved at the time of use into apyrogenic sterile water, serum or any other pharmaceutically acceptable vehicle. For use in the form of dry aerosols which are intended to be inhaled directly, the active principle is is finely divided and is combined with a solid, water-soluble vehicle or diluent with a particle size of 30 to 80 μm, for example dextran, mannitol or lactose.

In human therapy, the products according to the invention may be particularly useful in the treatment of pain of traumatic, post-surgical, menstrual or cephalic origin, in facial vascular pain (cluster headache) and in the treatment of migraine. The novel isoindole derivatives are also useful in the treatment of inflammation in rheumatology, in the treatment of rheumatoid arthritis and in complaints due to disruption of the immune system, in the treatment of inflammations in dermatology such as psoriasis, herpes, urticaria, eczema, photodermatosis, burns and in dental or ocular inflammatory complaints and in the field of lachrymal secretions; they are also useful in the treatment of painful and inflammatory spasmodic manifestations of the digestive system (ulcerous colitis, irritable bowel syndrome, Crohn's disease), the urinary system (urinary hyperreflexia, cystitis) and the respiratory system (asthma, bronchial hypersecretion, chronic bronchitis, thiniris) and in antiemetic treatments. The products according to the invention may also find an application in the treatment of neurological diseases, Parkinson's disease, Alzheimer's disease, in the treatment of inflammatory and/or autoimmune and/or demyellnating diseases of the central and/or peripheral nervous system (multiple sclerosis, polyradiculonephritis, encephalopathies of vital, etc., origin), in neurological syndromes related to a plasmatic extravasation (oedema of the spinal cord, cerebral oedema, etc.), in relation with an attack on the blood-brain barrier or in any spastic neurological syndrome (muscle-relaxing treatments). The products according to the invention may also be useful in the treatment of anxiety, psychosis, schizophrenia, or alternatively in cardiovascular disorders such as hypotension. Another application may also be the treatment of gynaecological disorders, the treatment of disorders linked to poor growth regulation (dwarfism, hypotrophy secondary to chronic infant diseases, osteoporosis, the development of grafts).

The doses depend upon the desired effect and the duration of the treatment. For an adult, they are generally between 0.25 and 1500 mg per day in graded doses.

Generally speaking, the doctor will determine the dosage which he considers to be the most suitable, depending on the age, weight, and all the other personal factors of the subject to be treated.

The example which follows, given without any limitation being implied, illustrates a composition according to the invention.

Example

Tablets of active product and having the following composition are prepared according to the usual technique:

(3aRS,4RS,5RS,7aSR)-4-(2-methoxyphenyl)-2-[(2-methoxyphenyl)acetyl]-5-methyl-4-perhydroisoindolol 25 mg Starch 83 mg Silica 30 mg Magnesium stearate 3 mg

We claim:

1. A perhydroisoindole derivative of the following formula or a salt thereof:

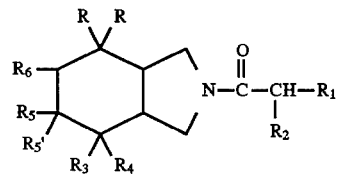

in which:

$R_1$ represents:

a phenyl radical that is unsubstituted or substituted with at least one substituent selected from:

a halogen atom or a hydroxyl radical, an alkyl radical that is unsubstituted or substituted with a halogen atom, an amino radical, an alkylamino radical, or a dialkylamino radical, an alkyloxy or alkylthio radical that is unsubstituted or substituted with a hydroxyl, an amino radical, an alkylamino radical or a dialkylamino radical, wherein said amino, alkylamino, and dialkylamino radicals are unsubstituted or substituted with a phenyl radical, a hydroxyl, an amino radical, or a dialkylamino radical wherein the alkyl parts thereof form, together with the nitrogen atom to which they are attached, a 5- or 6-membered heterocycle that may contain an additional hereto atom selected from oxygen, sulphur or nitrogen, wherein said 5- to 6-membered heterocycle is unsubstituted or substituted with an alkyl radical, a hydroxyl, an hydroxyalkyl radical, or an amino radical, an alkylamino radical or a dialkylamino radical wherein the alkyl parts form, together with the nitrogen atom to which they are attached, a 5- or 6-membered heterocycle as defined above, or a cyclohexadienyl radical, a naphthyl radical, an indenyl radical, or a saturated or unsaturated mono- or polycyclic heterocyclic radical containing from 5 or 9 carbon atoms and at least one hetero atom selected from oxygen, nitrogen or sulphur, wherein said saturated mono- or polycyclic radical is unsubstituted or substituted with a halogen atom, an alkyl radical or an alkyloxy radical;

$R_2$ represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical;

$R_3$ represents a phenyl radical that is:
unsubstituted or substituted in the 2-position with an alkyl radical or an alkyloxy radical, wherein said alkyl radical and said alkyloxy radicals contain 1 or 2 carbon atoms,
substituted in the 2-position with a fluorine atom, or
disubstituted with trifluoromethyl radicals;

$R_5$ and $R'_5$ are identical or different and are defined as follows: one of $R_5$ or $R'_5$ represents a hydrogen atom, a hydroxyl, or an alkyl radical and the other represents a hydrogen atom or an alkyl radical while $R_4$ represents a hydroxyl, or $R_4$ represents a fluorine atom if $R_5$ and $R'_5$ represent a hydrogen atom or an alkyl radical, or $R_4$ forms a bond with $R_5$;

$R_6$ represents a hydrogen atom, an alkyl radical, a hydroxyl, or a hydroxyalkyl radical; and one of said R substituents represents a hydrogen atom, an alkyl radical, a hydroxyl, or a hydroxyalkyl radical, and the other R substituent represents a hydrogen atom, an alkyl radical, a phenyl radical, or a hydroxyalkyl radical;

wherein said alkyl and acyl radicals contain, unless otherwise specified, from 1 to 4 carbon atoms in a straight or branched chain;

or a stereoisomeric form or racemate of the structure:

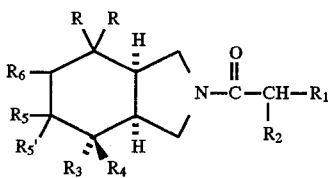

wherein —CHR$_1$R$_2$ chain is optically in the (R) or (S) forms, or a mixture of any of these forms.

2. A perhydroisoindole derivative according to claim 1, wherein $R_1$ is a saturated or unsaturated mono- or polycyclic heterocyclic radical selected from thienyl, furyl, pyridyl, dithiinyl, indolyl, isoindolyl, benzothienyl, thiazolyl, isothiazazolyl, oxazoyl, imidazolyl, pyrrolyl, triazolyl, thiadiazolyl, quinolyl, isoquinolyl, and naphthyridinyl.

3. A perhydroisoindole derivative according to claim 1, where $R_1$ represents a phenyl radical that is unsubstituted or substituted with a hydroxyl, an alkyloxy radical or a dialkylamino radical, or $R_1$ represents a saturated or unsaturated mono- or polycyclic heterocyclic radical containing from 5 to 9 carbon atoms and at least one hetero atom selected from the group consisting of oxygen, nitrogen and sulphur;

$R_2$ represents a hydrogen atom or an alkyl radical;

$R_3$ represents a phenyl radical that is unsubstituted or substituted in the 2-position with an alkyloxy radical containing from 1 to 2 carbon atoms or with a fluorine atom, or said phenyl radical is disubstituted with trifluoromethyl radicals;

$R_5$ and $R'_5$ are identical or different and one of $R_5$ and $R'_5$ represents a hydrogen atom or a hydroxyl or an alkyl radical, and the other $R_5$ and $R'_5$ represents a hydrogen atom or an alkyl radical;

$R_4$ represents a hydroxyl radical;

$R_6$ represents a hydrogen atom, an alkyl radical, a hydroxyl or a hydroxyalkyl radical; and one of said R substituents represents a hydrogen atom, an alkyl radical, a hydroxyl, or a hydroxyalkyl radical and the other R substituent represents a hydrogen atom or an alkyl or phenyl radical.

4. A perhydroisoindole derivative according to claim 1, which is 7,7-dimethyl-4-(2-methoxyphenyl)-2-[2-(S)-(2-methoxyphenyl)propionyl]-4,5-perhydroisoindolediol.

5. A perhydroisoindole derivative according to claim 1, which is 4-(2-methoxyphenyl)-2-[2-(S)-(2-methoxyphenyl)proponyl]-5-methyl-4-perhydroisoindolol.

6. A perhydroisoindole derivative according to claim 1, which is 2-[2-(S)-(2-hydroxyphenyl)propionyl]-4-(2-methoxyphenyl)-6-methyl-4-perhydroisoindolol.

7. A perhydroisoindole derivative according to claim 1, which is 7-(hydroxymethyl)-4-(2-methoxyphenyl)-2-[2-(S)-(2-methoxyphenyl)propionyl]-7-methyl-4-perhydroisoindolol.

8. A perhydroisoindole derivative according to claim 1, which is 7-(hydroxymethyl)-2-(3-indolylacetyl)-4-(2-methoxyphenyl)-7-methyl-4-perhydroisoindolol.

9. A process for preparing a perhydroisoindole derivative according to claim 1, which comprises the steps of:

reacting an acid or a reactive derivative of an acid of formula:

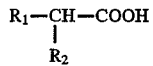

in which $R_1$ and $R_2$ are defined as in claim 1, with an isoindole derivative of formula:

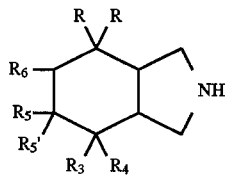

in which R, $R_3$, $R_4$, $R_5$, $R'_5$ and $R_6$ are defined as in claim 1, optionally converting the product of said reacting step in which $R_4$ is a hydroxyl radical and $R_5$ is a hydrogen atom or an alkyl radical to a second product in which $R_4$ is a fluorine atom and $R_5$ is a hydrogen atom or an alkyl radical or in which $R_4$ and $R_5$ together form a bond, and then optionally converting said second product to a salt.

10. A process for preparing a perhydroisoindole derivative according to claim 1, which comprises the steps of:

reacting an organometallic compound of formula:

in which $R_3$ is defined as in claim 1, and M represents lithium, a MgX radical or a $CeX_2$ radical in which X is a halogen atom, with a perhydroisoindolone derivative of formula:

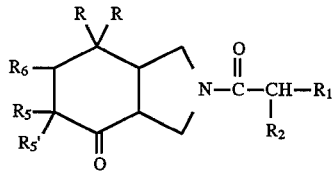

in which $R_1$, $R_2$, $R_5$, $R'_5$, $R_6$ and R are defined as in claim 1, to form an alcohol, then, either converting the alcohol obtained from said reacting step to a perhydroisoisondole derivative in which $R_4$ is a fluorine atom and $R_5$ is a hydrogen atom or an alkyl radical or to a perhydroisoindole derivative in which $R_4$ and $R_5$ together form a bond, or removing the radical protecting $R_5$; and then optionally separating the isomers produced and/or converting the product obtained to a salt.

11. A process for preparing a perhydroisoindole derivative according to claim 10, wherein the hydroxyl radicals of said perhydroisoindolone derivative are protected prior to said reacting step.

12. A process for preparing a perhydroisoindole derivative according to claim 1 in which one of the R substituents is a hydroxyl radical, $R_4$ represents a hydroxyl radical and at least one of $R_5$ or $R'_5$ is a hydrogen atom, which process comprises the steps of: reacting a perhydroisoindolone derivative of formula:

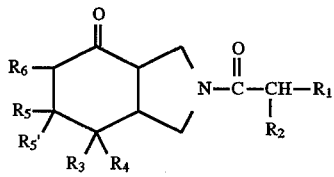

in which $R_1$, $R_2$, $R_3$ and $R_6$ are defined as in claim 1 and $R_4$, $R_5$ and $R'_5$ are defined as above, with an organometallic compound of general formula:

in which R is an alkyl radical or a phenyl radical, or a hydroxyalkyl radical in which the hydroxyl function is protected before said reacting step, and M represents lithium, a MgX radical or a $CeX_2$ radical in which X is a halogen atom, or reducting said perhydroisoindolone derivative to obtain a derivative according to claim 1 in which the other radical R is a hydrogen atom, and then, where appropriate, removing the protecting radicals.

13. A process for preparing a perhydoisoindole derivative according to claim 1 in which $R_5$ or $R'_5$ and $R_6$ are simultaneously hydroxyl radicals and each R is other than a hydrogen atom, which comprises the step of reacting osmium tetroxide with a perhydoisoindole derivative of formula:

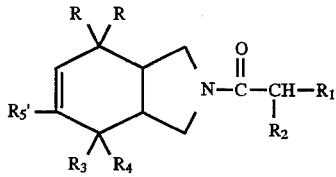

in which $R_1$, $R_2$, $R_3$, $R_4$, R and $R'_5$ are defined as in claim 1.

14. A perhydroisoindole derivative of the formula:

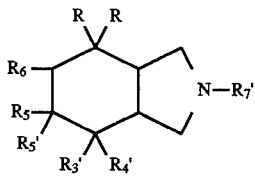

or a salt thereof, in which R, $R_5$, $R'_5$ and $R_6$ are defined as in claim 1, $R'_3$ and $R'_4$ are defined as $R_3$ and $R_4$ in claim 1, or together form an oxo radical, and $R'_7$ is a hydrogen atom or represents an amino-protecting radical;

a racemic form of said derivative, a stereoisomeric form of said derivative, or a mixture of any of these forms.

15. A perhydroisoindole derivative according to claim 14, wherein said $R'_7$ is an amino-protecting radical and is selected from alkyloxycarbonyl, benzyloxycarbonyl, benzyl that is unsubstituted or substituted, formyl, chloroacetyl, trichloroacetyl, trifluoroacetyl, vinyloxycarbonyl, phenoxycarbonyl, 1-chloroethoxycarbonyl and chlorocarbonyl groups.

16. A pharmaceutical composition, which comprises a pharmaceutically effective amount of at least one derivative according to claim 1 and at least one pharmaceutically acceptable carrier.

17. A pharmaceutical composition, which comprises a pharmaceutically effective amount of at least one perhydroisoindole derivative according to claim 1, and at least one NK2-receptor antagonist in combination with at least one pharmaceutically acceptable carrier.

* * * * *

UNITED STATES PATENT AND TRADEMARK OFFICE
CERTIFICATE OF CORRECTION

PATENT NO. : 5,624,950
DATED : April 29, 1997          Sheet 1 of 3
INVENTOR(S) : Daniel ACHARD et al.

It is certified that error appears in the above-indentified patent and that said Letters Patent is hereby corrected as shown below:

On the Title Page, Item [57], in the Abstract,
in the formula, "$R_5'$" should read --$R'_5$--.

Column 1, line 15, in the formula;
Column 2, line 60, in the formula;
Column 3, line 17, in the formula;
Column 4, line 64, in the formula;
Column 5, line 33, in the formula;
Column 6, line 5, in the formula; and
        line 37, in the formula;
Column 7, line 7, in the formula;
        line 48, in the formula; and
        line 64, in the formula;
Column 8, line 14, in the formula; and
        line 44, in the formula; and
Column 9, line 5, in the formula; and
        line 23, in the formula,
  "$R_5'$" should read --$R'_5$--.

UNITED STATES PATENT AND TRADEMARK OFFICE
CERTIFICATE OF CORRECTION

PATENT NO. : 5,624,950
DATED : April 29, 1997
INVENTOR(S) : Daniel ACHARD et al.

It is certified that error appears in the above-indentified patent and that said Letters Patent is hereby corrected as shown below:

Claim 1, column 47, line 60, after "wherein" insert --the--, and "optically" should read --optionally--.

Claim 2, column 47, line 66, "isothiazazolyl" should read --isothiazolyl--, and "oxazoyl" should read --oxazolyl--.

Claim 5, column 48, line 33, "proponyl" should read --propionyl--.

Claim 10, column 49, line 27, "perhydroisoisondole" should read --perhydroisoindole--.

Claim 12, column 50, line 4, "reducting" should read --reducing--.

UNITED STATES PATENT AND TRADEMARK OFFICE
CERTIFICATE OF CORRECTION

PATENT NO. : 5,624,950
DATED : April 29, 1997      Sheet 3 of 3
INVENTOR(S) : Daniel ACHARD et al.

It is certified that error appears in the above-indentified patent and that said Letters Patent is hereby corrected as shown below:

Claim 1, column 46, line 50, in the formula;
      column 47, line 57, in the formula;
Claim 9, column 48, line 61, in the formula;
Claim 10, column 49, line 21, in the formula;
Claim 12, column 49, line 50, in the formula;
Claim 13, column 50, line 20, in the formula; and
Claim 14, column 50, line 32, in the formula,
"$R_5'$" should read --$R'_5$--.

Signed and Sealed this

Twenty-eighth Day of April, 1998

*Attest:*

*Attesting Officer*

BRUCE LEHMAN
*Commissioner of Patents and Trademarks*